Figure 3A:
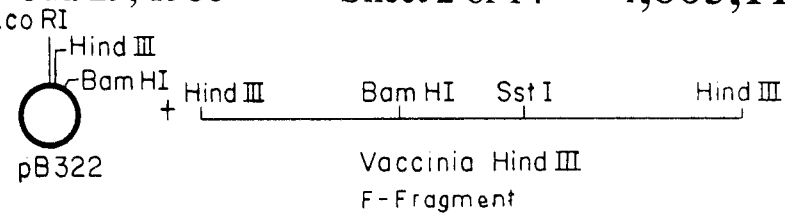

United States Patent [19]

Paoletti et al.

[11] Patent Number: 4,603,112
[45] Date of Patent: Jul. 29, 1986

[54] MODIFIED VACCINIA VIRUS

[75] Inventors: Enzo Paoletti, Delmar; Dennis Panicali, Averill Park, both of N.Y.

[73] Assignee: Health Research, Incorporated, Albany, N.Y.

[21] Appl. No.: 446,824

[22] Filed: Dec. 8, 1982

Related U.S. Application Data

[63] Continuation-in-part of Ser. No. 334,456, Dec. 24, 1981.

[51] Int. Cl.$^4$ .................. C12N 7/00; C12N 15/00
[52] U.S. Cl. .................. 435/235; 435/172.1; 435/172.2; 435/172.3; 424/89
[58] Field of Search .................. 435/235, 238, 172.1, 435/172.2, 172.3

[56] References Cited

PUBLICATIONS

Panicali et al., "Two Major DNA Variants etc.", J. Virol. 37(3), 1981, 1000–1010.
Weir et al., "Mapping of the Vaccinia Virus etc.", Proc. Nat'l. Acad. Sci. USA 79, 1982, 1210–1214.
Nakano et al., "Molecular Genetics of Vaccinia etc.", Proc. Nat'l. Acad. Sci. USA 79, 1982, 1593–1596.
Panicali et al., "Construction of Poxviruses etc.", Proc. Nat'l. Acad. Sci. USA 79, 1982, 4927–4931.
Mackett et al., "Vaccinia Virus etc.", Proc. Nat'l. Acad. Sci. USA 79, 1982, 7415–7419.
Smith et al., "Infectious Vaccinia Virus Recombinants etc.", Nature 302, 1983, 490–495.
Panicali et al., "Construction of Live Vaccines etc.", Proc. Nat'l. Acad. Sci. USA 80, 1983, 5364–5368.
Ensinger et al., "Marker Rescue etc.", J. Virol. 48(2); 1983, 419–428.
Smith et al., "Construction and Characterization etc.", Proc. Nat'l. Acad. Sci. USA 80, 1983, 7155–7159.
Jones et al., "Mapping of the Vaccinia Virus etc.", J. Virol. 49(1), 1984, 72–77.
Paoletti et al., "Construction of Live Vaccines etc.", Proc. Nat'l. Acad. Sci. USA 81, 1984, 193–197.
Mocarski et al.-Cell, vol. 22, (1980) p. 243.
Morse et al.-J. Virol., vol. 26, (1978) p. 389.
Bossart et al.-Chem. Abst., vol. 89, (1978) p. 56,251n.
Katz et al.-Chem. Abst., vol. 89, (1978) p. 39,241s.
Sam et al.-Ann. Virol., vol. 132E, (1981) pp. 135–150.
Wigler et al.-Cell, vol. 11, (1977) pp. 223–232.
Moss et al.-J. of Virology, vol. 40, No. 2, Nov. 1981, pp. 387–389, & 393–395.
Shigeru et al., C.A. 86 #3119g, 1977 of Yakugaku Zasshi (1976)96(10): 1247–1254, Protein Inhibitors of Gastric Acid Secretion Isolated From Vaccinia Virus-Infected Tissues.
Shigeru, C.A. 88 #55061t, 1978 of Japan Kokai 77116402, 29 Sep. 1977, Gastric Juice Secretion-Inhibiting Protein From Vaccinia Virus Infected Animal Tissues.
Nippon Zoki Pharm. C.A. 94 #7711g, (1981) of Jpn. Kokai Tokkyo Koho 8087724, 2 Jul. 1980, Selective Immune Enhancer.
Kruczek-Juszczyk C.A. 92 #126795f, (1980) of Ann. Univ. Mariae Curie Sect. C, 1978, 33: 1–8, Interferon Induction by Viral Nucleic Acids in Chick Embryo Fibroblasts.
Panicali et al., C.A. 94 #135967g, 1981 of J. Virol., 1981, 37(3): 1000–10, Two Major DNA Variants Present in Serially Propagated Stocks of the WR Strain of Vaccinia Virus.
Katz et al., C.A. 89 #39241s, (1978) of J. Antimicrob. Chemother. 1978 4(2): 159–162, Genetic Recombination Between Temperature Sensitive Mutant and IBT Resistant Mutant of Vaccinia Virus.
Chem. Abstracts, 10th Coll. Index, (1977–1981), vols. 86–95, Virus, Animal, Vaccinia Virus.

*Primary Examiner*—Sam Rosen
*Attorney, Agent, or Firm*—Curtis, Morris & Safford

[57] ABSTRACT

What are disclosed are methods for modifying the genome of vaccinia virus to produce vaccinia mutants, particularly by the introduction into the vaccinia genome of exogenous DNA; modified vaccinia prepared by such methods; certain DNA sequences and unmodified and genetically modified microorganisms involved as intermediates in such methods; and methods for infecting cells and host animals with such vaccinia mutants to provoke the amplification of exogenous DNA and proteins encoded by the exogenous DNA, including antigenic proteins, by said cells and host animals.

12 Claims, 15 Drawing Figures

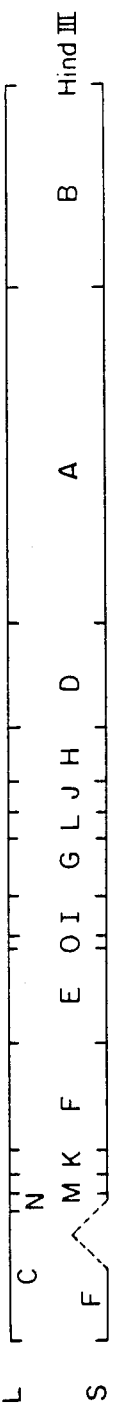
FIG. 1
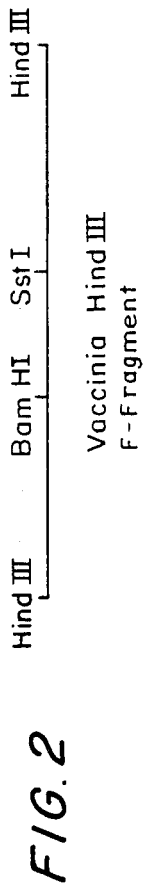
FIG. 2
| GENE | GROWTH IN NORMAL MEDIUM? | GROWTH IN HAT MEDIUM? | GROWTH IN BUdR? |
|---|---|---|---|
| TK+ | YES | YES | NO |
| TK- | YES | NO | YES |
FIG. 5

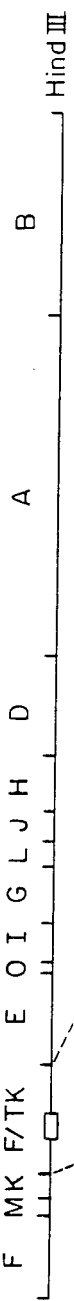
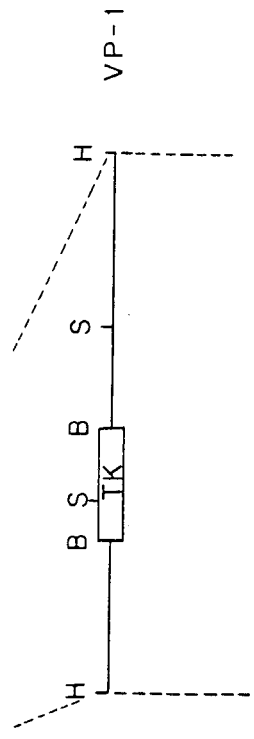
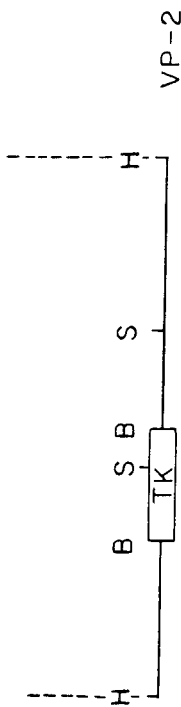
FIG. 4A
FIG. 4B
FIG. 4C

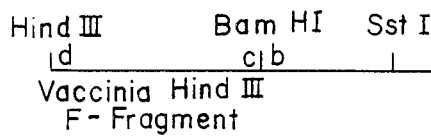
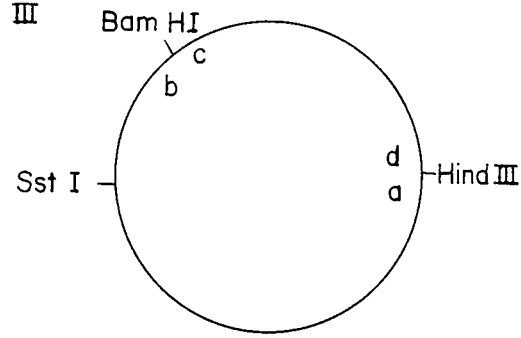
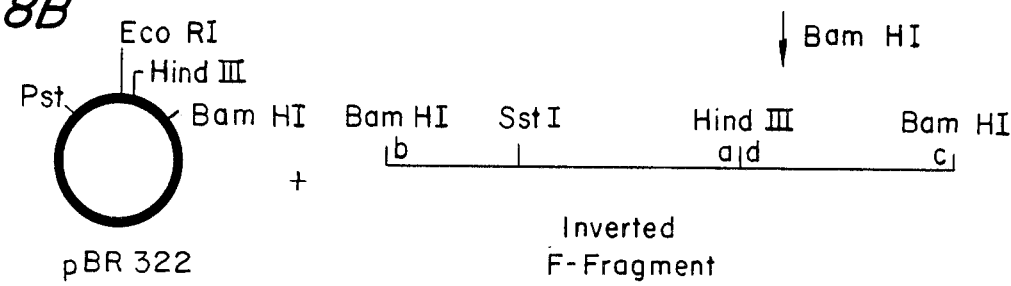
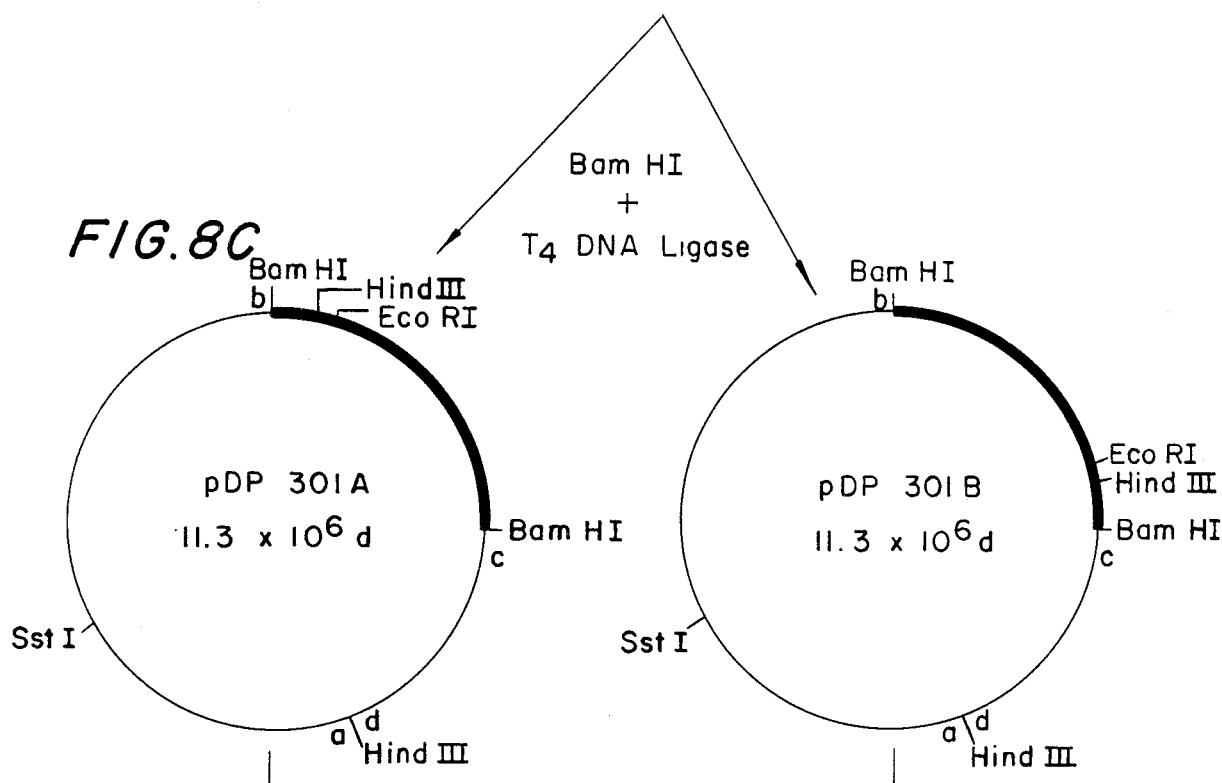
FIG. 8A
FIG. 8B
FIG. 8C
FIG. 8D

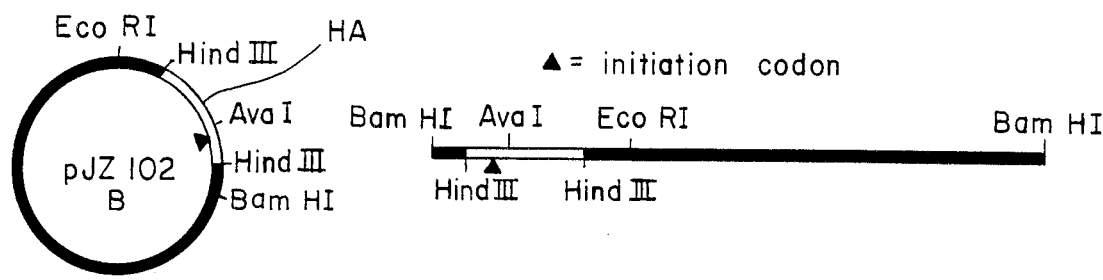
FIG.9A
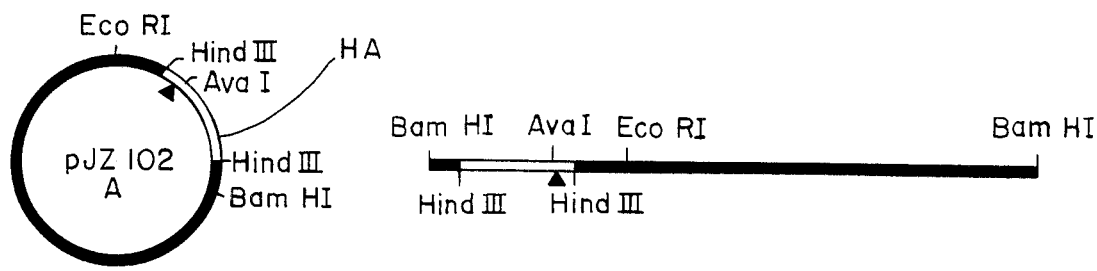
FIG.9B
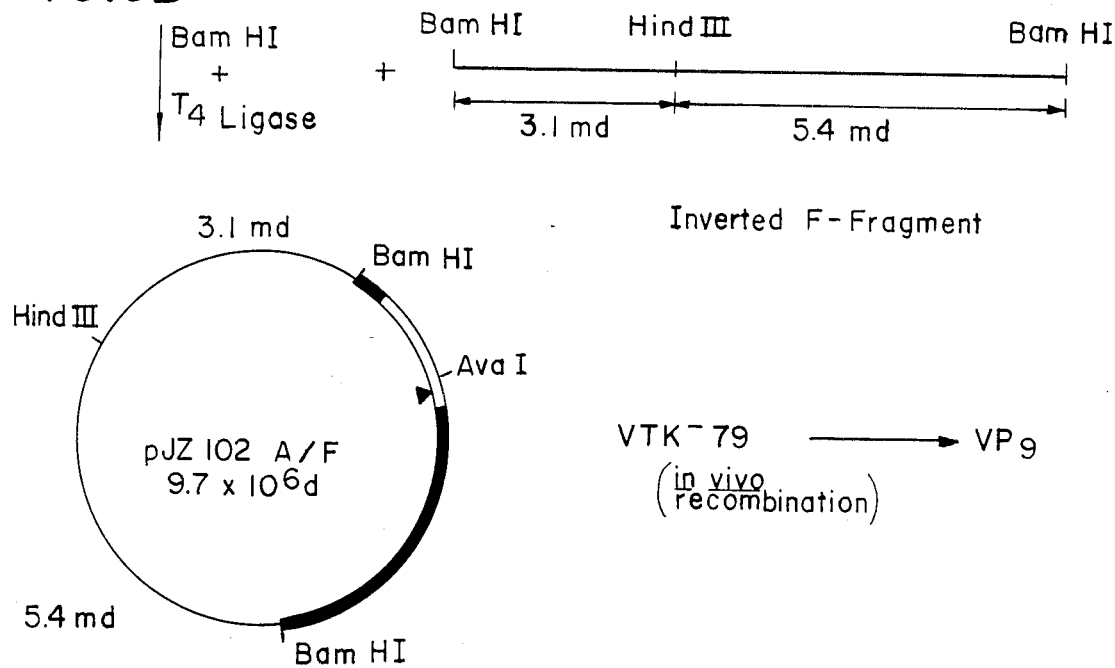
FIG.9C
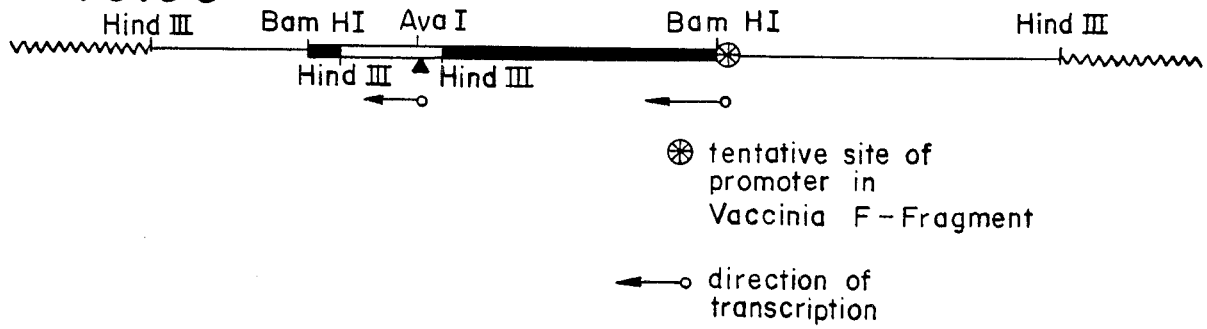

+

VP 7

↓ (in vivo recombination)

⊛ tentative site of promoter in Vaccinia F-Fragment

VP 10

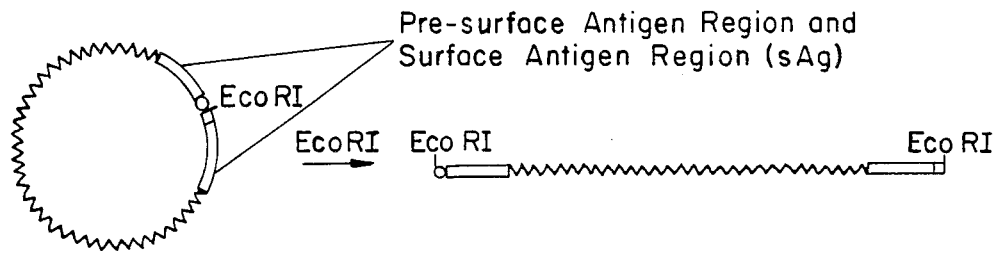
FIG. 11A
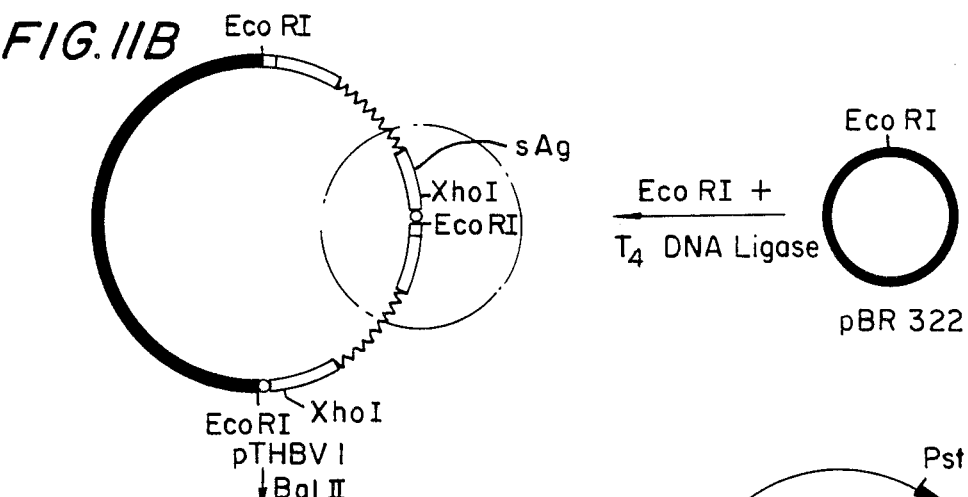
FIG. 11B
FIG. 11C
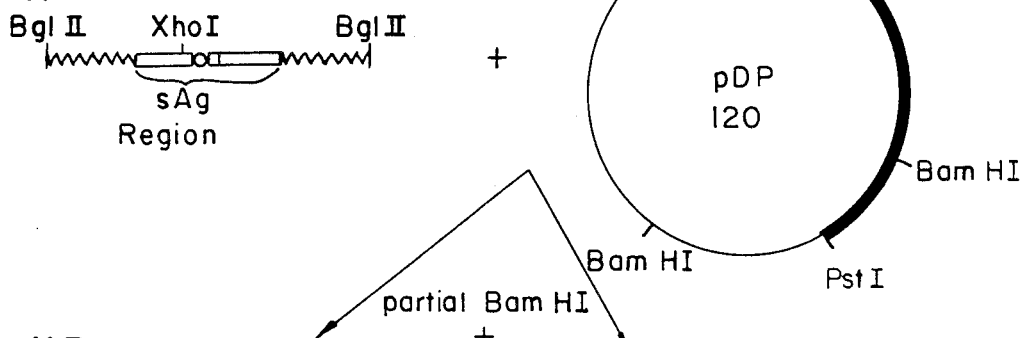
FIG. 11D
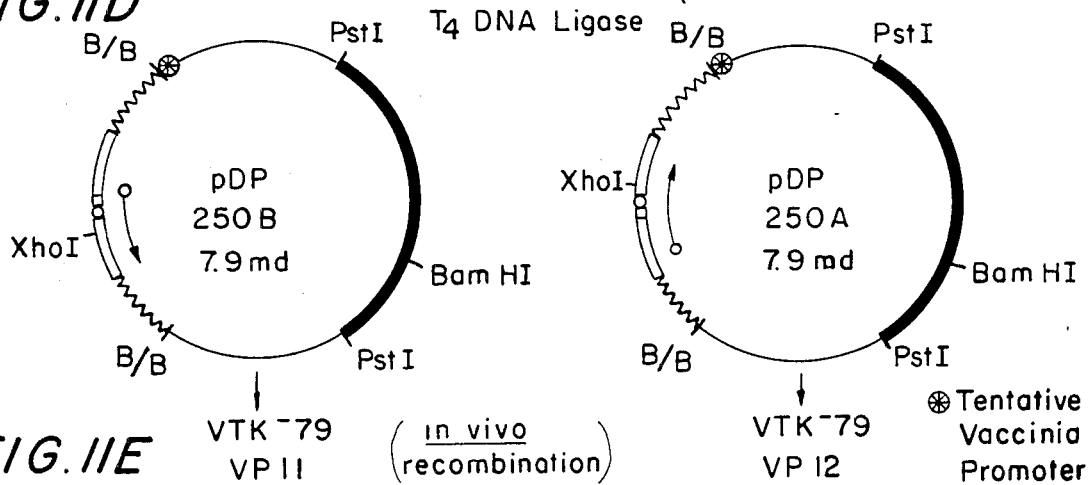
FIG. 11E FIG.12A
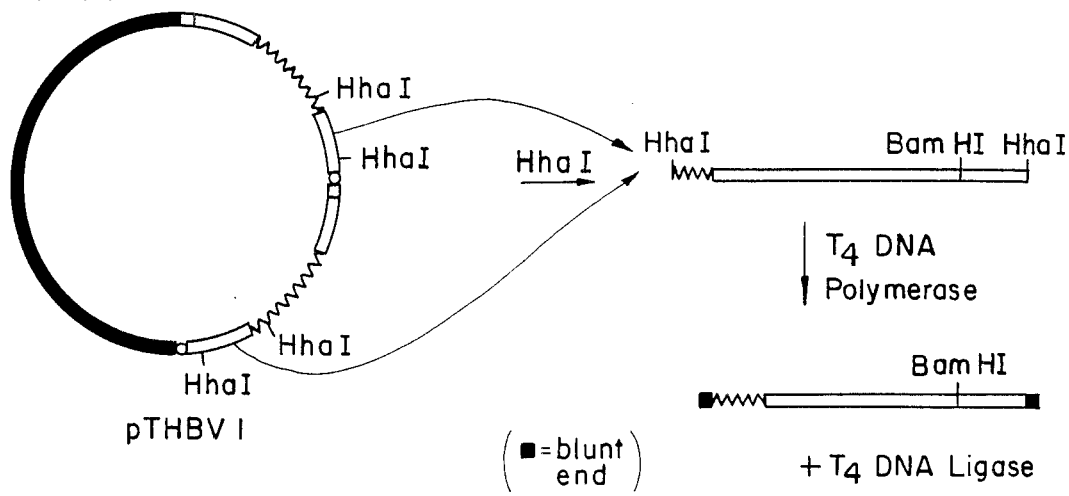
pTHBV I
FIG.12B
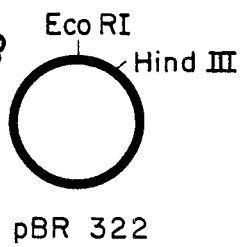
pBR 322
FIG.12C
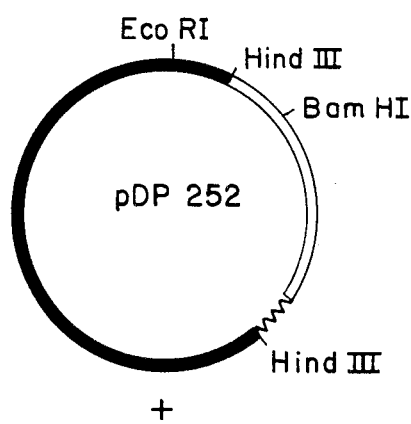
VP8
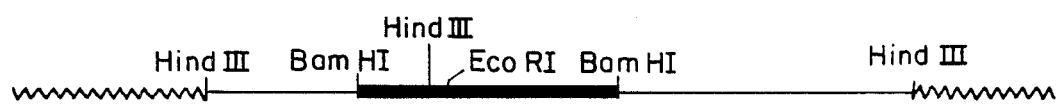
FIG.12D
VP 13

FIG.13A  EcoRI Fragment F of Herpes Virus Type I (strain KOS)
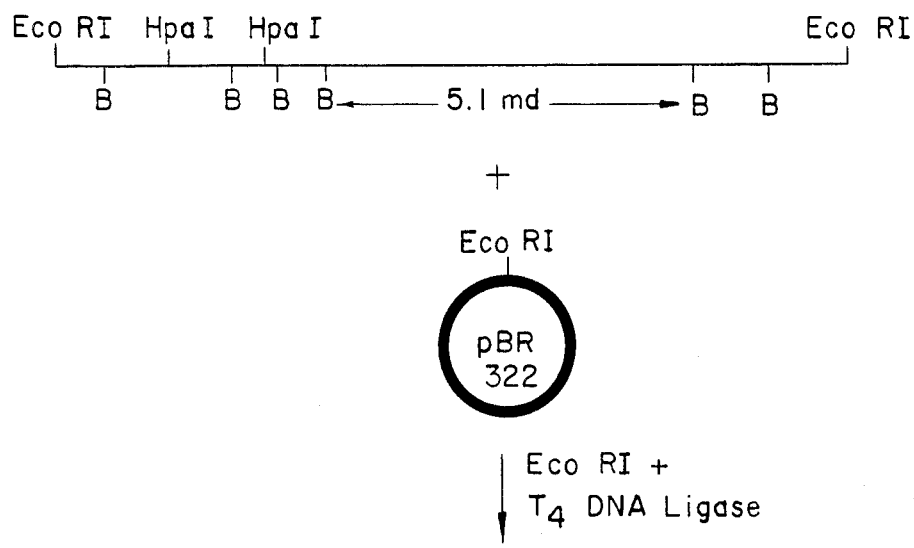
FIG.13B
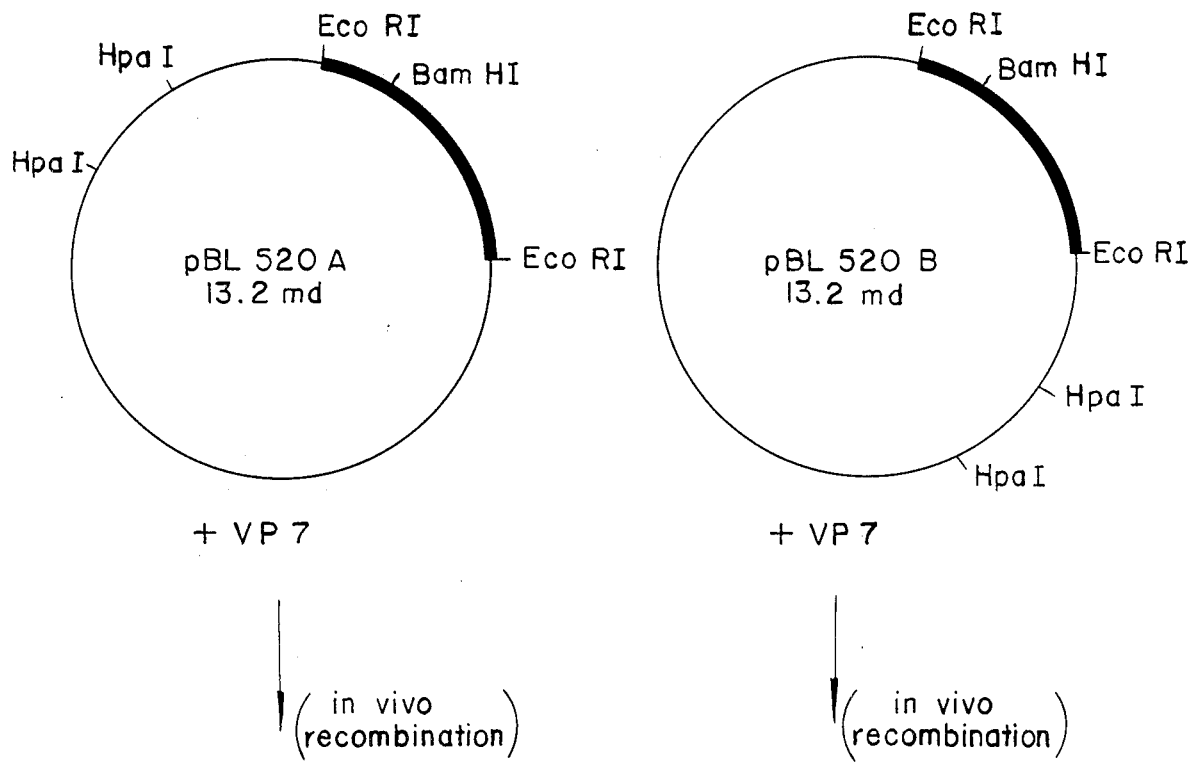
FIG.13C            VP 16                        VP 14

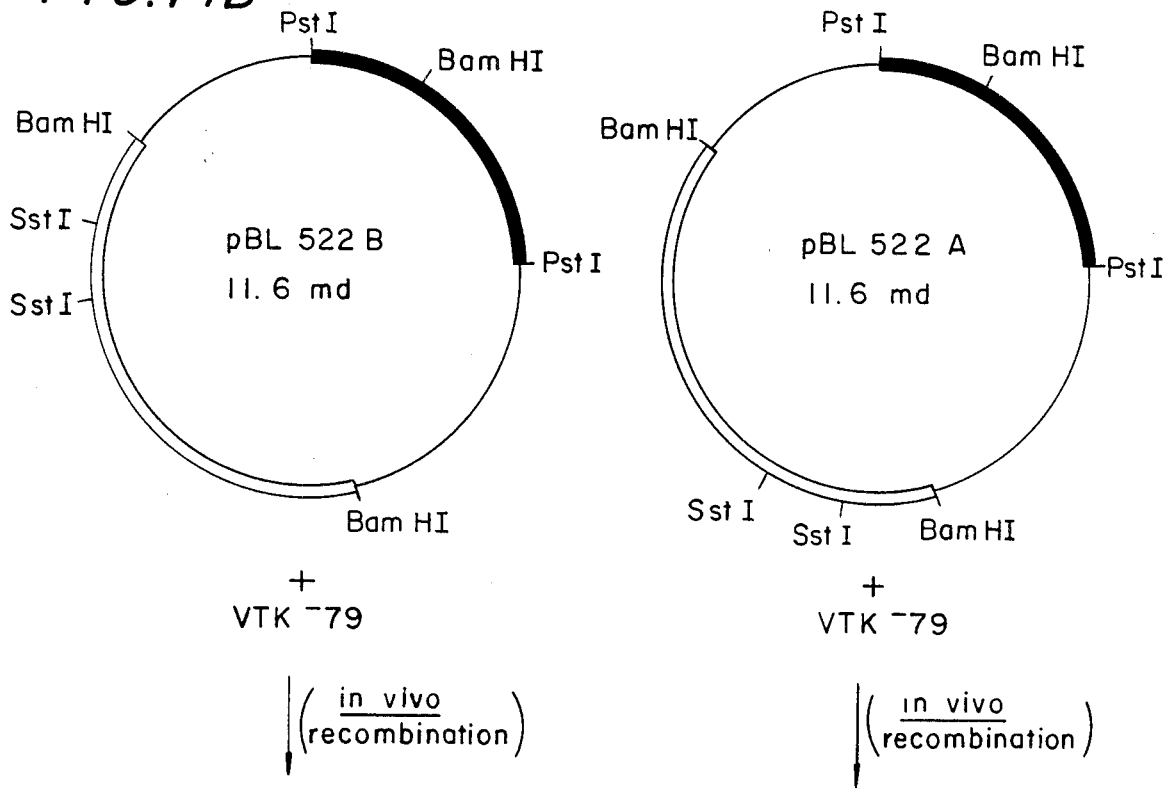
FIG. 14A  HSV BamHI G-Fragment
FIG. 14B  pBL 522 B 11.6 md / pBL 522 A 11.6 md
FIG. 14C  VP 18 / VP 17

MODIFIED VACCINIA VIRUS

The invention described herein was made with the support of the Federal Government and the Federal Government has certain rights in the invention.

This is a continuation-in-part of application Ser. No. 334,456 filed Dec. 24, 1981.

The present invention relates to modified vaccinia virus, to methods of making and using the same, and to other modified and unmodified microorganisms, and to certain DNA sequences, produced or involved as intermediates in the production of modified vaccinia virus. More in particular, the invention relates to vaccinia virus in which the naturally occurring genome of the virus has been altered ("vaccinia mutants") and to methods of making and using such vaccinia mutants, as well as to other unmodified and genetically modified microorganisms, and to certain DNA sequences, produced or involved as intermediates in the production of vaccinia mutants.

Vaccinia virus is the prototypic virus of the pox virus family and, like other members of the pox virus group, is distinguished by its large size and complexity. The DNA of vaccinia virus is similarly large and complex. Vaccinia DNA is about 120 megadaltons in size, for instance, compared with a DNA size of only 3.6 megadaltons for simian virus 40 (SV40). The DNA molecule of vaccinia is double-stranded and terminally cross-linked so that a single stranded circle is formed upon denaturation of the DNA. Vaccinia DNA has been physically mapped using a number of different restriction enzymes and a number of such maps are presented in an article by Panicali et al., J. Virol. 37, 1000–1010 (1981) which reports the existence of two major DNA variants of the WR strain of vaccinia virus (ATCC No. VR 119), which strain has been most widely used for the investigation and characterization of pox viruses. The two variants differ in that the S("small") variant (ATCC No. VR 2034) has a 6.3 megadalton deletion not occurring in the DNA of the L("large") variant (ATCC No. VR 2035). Maps obtained by treatment of the variants with the restriction enzymes Hind III, Ava I, Xho I, Sst I, and Sma I are presented in the aforementioned article.

Vaccinia, a eukaryotic virus, reproduces entirely within the cytoplasm of a host cell. It is a lytic virus, i.e. a virus, the replication of which in a cell results in lysis of the cell. The virus is considered non-oncogenic. The virus has been used for approximately 200 years in vaccines for inoculation against smallpox and the medical profession is well acquainted with the properties of the virus when used in a vaccine. Although inoculation with vaccinia is not without risk, the risks are on the whole well known and well defined and the virus is considered relatively benign.

At the heart of the present invention is the modification of the naturally occurring vaccinia genome to produce vaccinia mutants by rearrangement of the natural genome, by the removal of DNA from the genome, and/or by the introduction into the naturally occurring vaccinia genome of DNA which disrupts the naturally occurring genome ("foreign DNA"). Such foreign DNA may be naturally occurring in vaccinia or may be synthetic or may be naturally occurring in an organism other than vaccinia. If genetic information is present in this foreign DNA, the potential exists for the introduction of this information into a eukaryote via modified vaccinia virus. That is, the modified virus represents a relatively innocuous eukaryotic cloning vector from which genetic information has been deleted, or into which information has been inserted, or in which genetic information has been rearranged. Since the virus replicates wihin the cytoplasm of an infected cell, modified vaccinia virus represents a unique eukaryotic cloning vector unlike any other so far considered or currently under investigation.

This discovery has a number of useful consequences, among which are (A) novel methods for vaccinating mammals susceptible to vaccinia to induce in them an antibody response to antigens coded for by foreign DNA inserted into the vaccinia virus, (B) novel methods for the production by eukaryotic cells of biological products other than antigens, and (C) novel methods for the introduction into human or animal individuals or populations of missing genes or of genetic material for the modification, replacement, or repair of defective genes in the individuals or populations.

Suitably modified vaccinia mutants carrying exogenous genes which are expressed in a host as an antigenic determinant eliciting the production by the host of antibodies to the antigen represent novel vaccines which avoid the drawbacks of conventional vaccines employing killed or attenuated live organisms. Thus, for instance, the production of vaccines from killed organisms requires the growth of large quantities of the organisms followed by a treatment which will selectively destroy their infectivity without affecting their antigenicity. On the other hand, vaccines containing attenuated live organisms always present the possibility of a reversion of the attenuated organism to a pathogenic state. In contrast, when a modified vaccinia mutant suitably modified with a gene coding for an antigenic determinant of a disease-producing organism isused as a vaccine, the possibility of reversion to a pathogenic organism is avoided since the vaccinia virus contains only the gene coding for the antigenic determinant of the disease producing organism and not those genetic portions of the organism responsible for the replication of the pathogen.

The present invention offers advantages even with respect to new technology employing genetic engineering involving the production of an antigen by a recombinant prokaryotic organism containing a plasmid expressing a foreign antigenic protein. For instance, such technology requires the production of large amounts of the recombinant prokaryotic cells and subsequent purification of the antigenic protein produced thereby. In contrast, a modified vaccinia virus used for inoculation according to the present invention replicates within the inoculated individual to be immunized, thereby amplifying the antigenic determinant in vivo.

A further advantage of the use of vaccinia mutants as vectors in eukaryotic cells as vaccines or for producing biological products other than antigens is the possibility for post-translational modifications of proteins produced by the transcription of exogenous genes introduced into the cell by the virus. Such post-translational modifications, for instance glycosylation of proteins, are not likely in a prokaryotic system, but are possible in eukaryotic cells where additional enzymes necessary for such modifications are available. A further advantage of the use of vaccinia mutants for inoculation is the possibility of amplification of the antibody response by the incorpation, into the mutant, of tandem repeats of the gene for the antigen or of additional genetic elements which stimulate the immune response, or by the use of a strong promoter in the modified virus. A similar advantage holds in the production of biological products other than antigens.

Returning to a more detailed consideration of the vaccinia genome, the cross-linked double strands of the DNA are characterized by inverted terminal repeats each approximately 8.6 megadaltons in length, representing about 10 kilobasepairs (kbp). Since the central portions of the DNA of all pox viruses are similar, while the terminal portions of the viruses differ more strongly, the responsibility of the central portion for functions common to all the viruses, such as replication, is suggested, whereas th terminal portions appear responsible for other characteristics such as pathogenicity, host range, etc. If such a genome is to be modified by the rearrangement or removal of DNA fragments therefrom or the introduction of exogenous DNA fragments thereinto, while producing a stable viable mutant, it is evident that the portion of the naturally-occurring DNA which is rearranged, removed, or disrupted by the introduction of exogenous DNA thereinto must be non-essential to the viability and stability of the host, in this case the vaccinia virus. Such non-essential portions of the genome have been found to be present in the WR strain of vaccinia virus, for instance within the region present within the L-variant but deleted from the S-variant or within the Hind III F-fragment of the genome.

The modification of vaccinia virus by the incorporation of exogenous genetic information can be illustrated by the modification of the WR strain of vaccinia virus in the Hind III F-fragment thereof to incorporate into that fragment a gene of herpes simplex virus type I (HSV) responsible for the production of thymidine kinase (TK). TK is an enzyme which phosphorylates the nucleoside thymidine to form the corresponding monophosphorylated nucleotide which is subsequently incorporated into DNA.

The HSV TK gene represents DNA foreign to vaccinia virus which is convenient to introduce into vaccinia according to the present invention for a number of reasons. First, the gene is relatively readily available present in a herpes simplex virus DNA fragment that is produced by digestion with Bam HI endonuclease, as reported by Colbere-Garapin et al. in Proc. Natl. Acad. Sci. USA 76, 3755–3759 (1979). Second, this HSV Bam HI fragment has been introduced into plasmids and into eukaryotic systems in the prior art, for instance as reported by Colbere-Garapin et al., loc. cit. and by Wigler et al., Cell 11, 223–232 (1977). Third, experience has shown that if HSV TK can be introduced as an exogenous gene into a eukaryotic system, and is expressed— which requires unambiguous and faithful translation and transcription of the genetic locus—, then other exogenous genes can similarly be introduced and expressed.

In the following text, reference is made to a number of microorganisms, both known and novel, most of which are deposited in a public repository and have been given identification numbers. These microorganisms and their repository numbers are tabulated below for sake of convenient reference:

| ORGANISM | ATCC NO. |
|---|---|
| WR strain of vaccinia virus | VR 119 |
| WR strain of vaccinia virus, | VR 2034 |
| S-variant | |
| WR strain of vaccinia virus, | VR 2035 |
| L-variant | |
| Syrian hamster kidney cells | CCL-10 |
| CV-1 cells | CCL-70 |
| VP-3 | VR 2036 |
| VP-4 | VR 2033 |
| VP-5 | VR 2028 |
| VP-6 | VR 2029 |
| VP-7 | VR 2042 |
| VP-8 | VR 2053 |
| VP-9 | VR 2043 |
| VP-10 | VR 2044 |
| VP-11 | VR 2045 |
| VP-12 | VR 2046 |
| VP-13 | VR 2047 |
| VP-14 | VR 2048 |
| VP-16 | VR 2050 |
| VP-17 | VR 2051 |
| VP-18 | VR 2052 |
| VP-22 | VR 2054 |
| VTK-79 | VR 2031 |
| VTK-79L | VR 2056 |

Figure 3B:
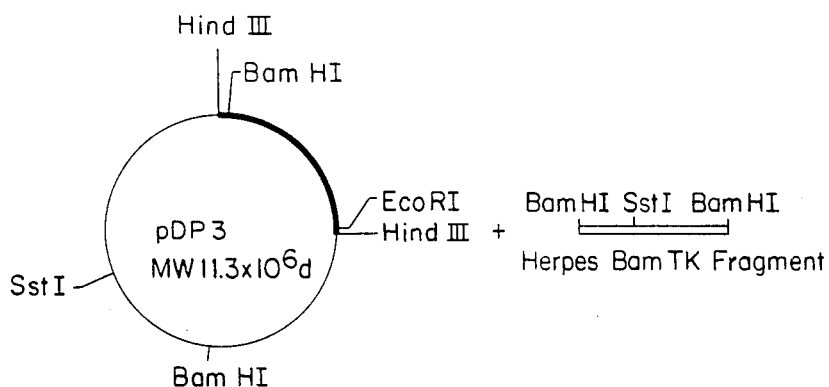
Figure 3C:
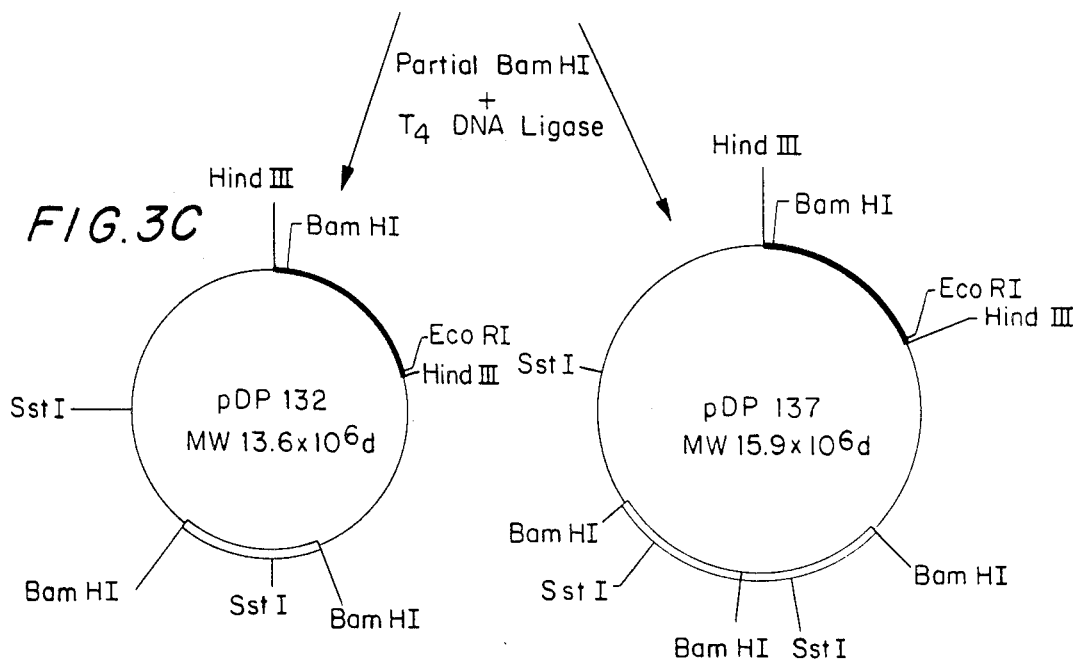
Figures 6A, 6B, 6C:
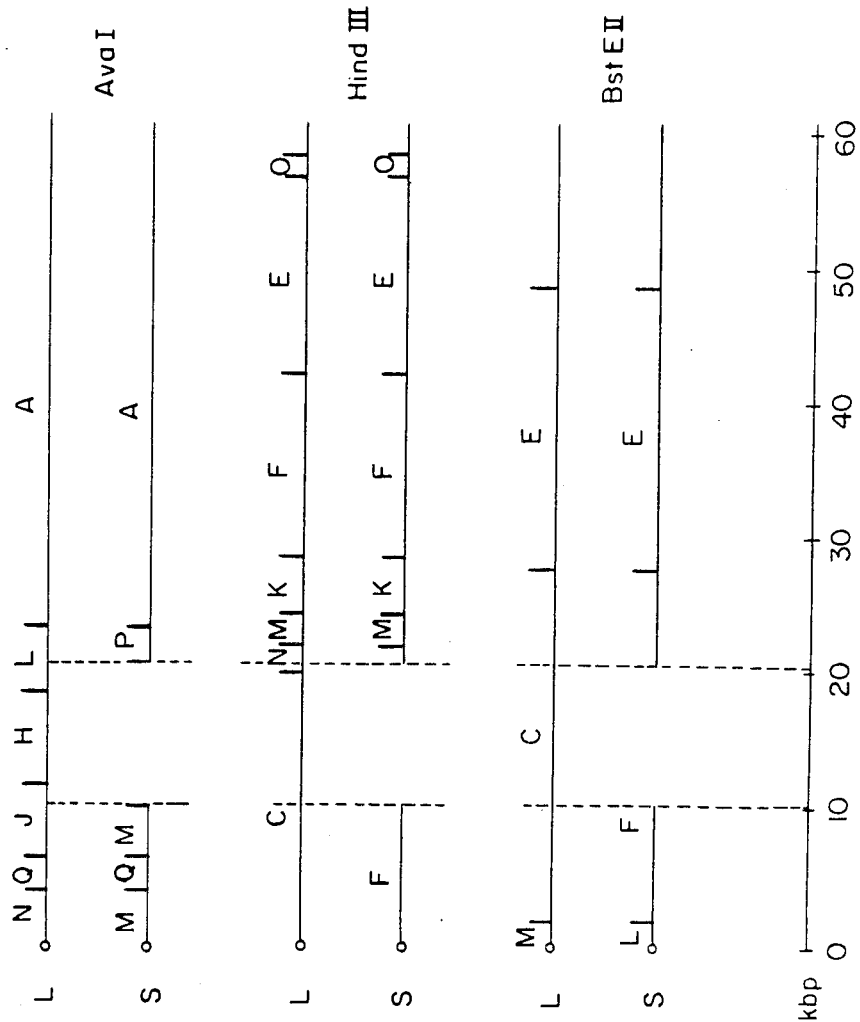

A better understanding of the present invention will be had by referring to the accompanying drawings, in which FIG. 1 is a map of the aforementioned L- and S-variants of the WR strain of vaccinia determined using Hind III as a restriction enzyme and showing the deletion of sequences in the terminal C fragment of the L-variant, which deletion is outside the terminal repeat section of the genome. The deleted DNA sequences are unique to the L structure and, since the growth of the S- and L-variants is identical, this deleted region must be non-essential;

FIG. 2 shows the vaccinia Hind III F-fragment in greater detail, including two further restriction sites therein, namely Sst I and Bam HI, at least the latter of which sites offers a locus at which exogenous DNA can be introduced into the vaccinia Hind III F-fragment without disturbing any essential vaccinia genes;

FIGS. 3A–C schematically show a method for the introduction of the HSV TK gene into the vaccinia Hind III F-fragment;

FIGS. 4A–C is a restriction map of certain vaccinia mutants produced according to the present invention and shows in detail the position of the HSV TK inserts present in the Hind III F-fragment in two such virus mutants, designated herein as VP-1 and VP-2;

FIG. 5 is a table summarizing certain techniques useful in screening possible recombinant viruses to determine the presence or absence of the HSV TK gene therein; and FIGS. 6A–C are restriction maps of the left-hand terminal portion of the vaccinia WR genome showing the relationship of various restriction fragments to the unique L-variant DNA sequence deleted from the corresponding S-variant.

Figure 7A:
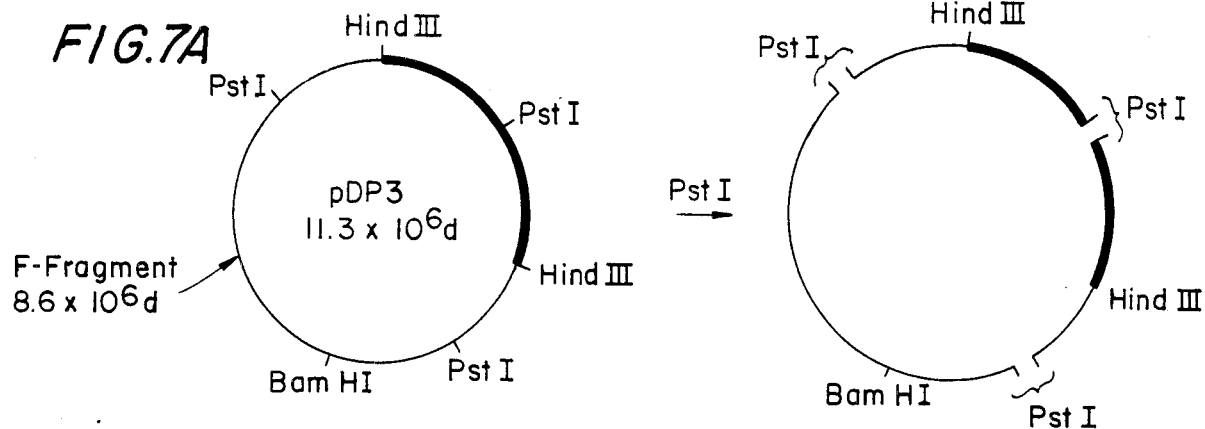
Figure 7B:
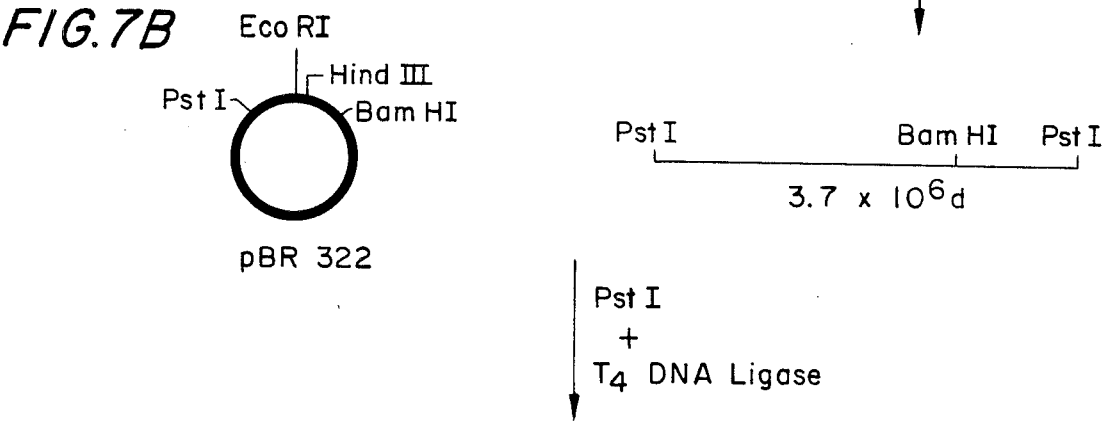
Figure 7C:
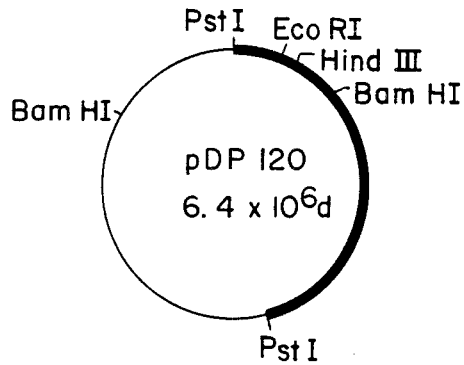

FIGS. 7A–C schematically show a method for constructing a new plasmid, pDP 120, which contains a portion of the vaccinia Hind III F-fragment combined with pBR 322, but which plasmid is of lower molecular weight than plasmid pDP 3, shown in FIG. 3B above.

FIGS. 8A–D schematically show the construction of two plasmids, pDP 301A and pDP 301B, which permit the incorporation of the DNA sequence of pBR 322 into vaccinia virus to produce vaccinia mutants VP 7 and VP 8.

FIGS. 9A–C schematically show the construction of a virus mutant, VP 9, into the genome of which the influenza hemagglutinin gene (HA) has been incorporated using a technique like that shown in FIGS. 8A–D.

Figure 10A:
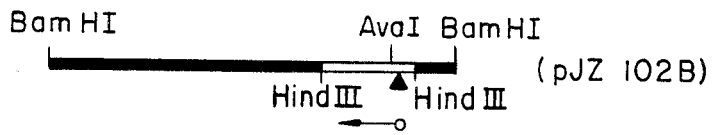
Figure 10B:
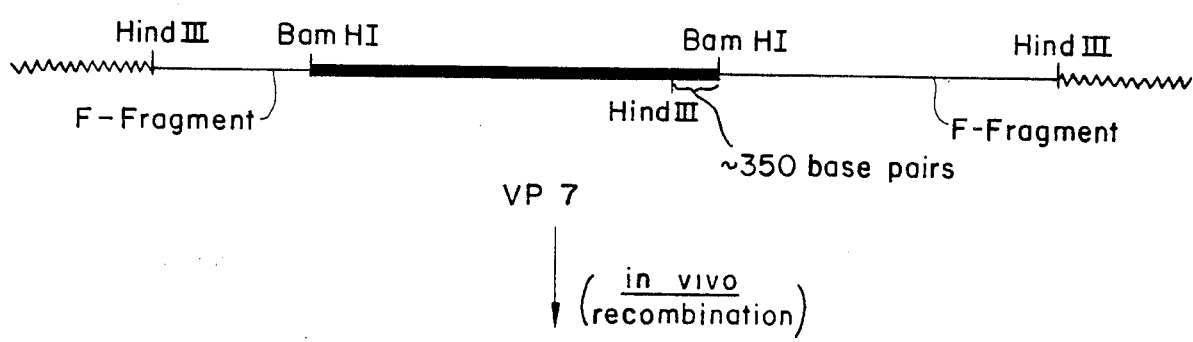
Figure 10C:
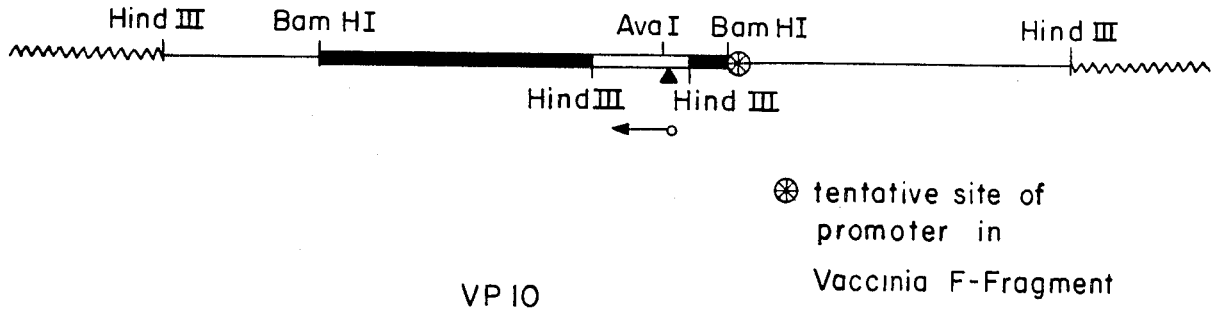

FIGS. 10A–C schematically shows the construction of a further vaccinia mutant, VP 10, also containing the influenza hemagglutinin (HA) gene, but prepared directly by in vivo recombination using VP 7.

FIGS. 11A–E show the construction of two vaccinia mutants, designated VP 11 and VP 12, each of which contains in its genome the DNA sequence coding for the surface antigen of hepatitis B virus incorporated thereinto by in vivo recombination of vaccinia virus VTK$^{-}$79 with, respectively, newly constructed plasmids pDP 250B and pDP 250A.

FIGS. 12A–D schematically show the construction of a new plasmid, pDP 252, which combines pBR 322 with a portion of the hepatitis B virus (HBV) genome, which portion is entirely within that region of the HBV region genome which codes for the surface antigen. The Figures show the introduction of the resulting pDP 252 plasmid into vaccinia mutant VP 8 with the resultant formation of a further vaccinia variant identified as VP 13.

FIGS. 13A–C show the construction of two further plasmids, pBL 520 A and pBL 520 B, and their insertion into VP 7 to produce two further vaccinia mutants, VP 16 and VP 14, each containing the DNA sequence of herpes virus I which codes for the production of herpes glycoproteins gA+gB, two of the principal immunogenic proteins of herpes simplex virus types I and II.

FIGS. 14A–C show the construction of two further plasmids, pBL 522 A and 522 B, incorporating the 5.1 md Bam HI fragment G shown in FIG. 13A as present in the Eco RI herpes F-fragment [De Luca et al., Virology 122, 411–423 (1982)].

FIGS. 15A–F show the construction of a further vaccinia variant, VP 22, in which foreign DNA, namely a herpes Bgl/Bam TK fragment, has been inserted into the vaccinia genome in a non-essential portion other than the F-fragment thereof.

Referring to FIG. 1, if the L- and S-variants of the vaccinia virus are subjected to the action of Hind III, a restriction enzyme well known in the prior art and commercially available, the virus genomes are respectively cleaved into 15 or 14 segments designated with the letters A through O, with the letter A used to designate the largest fragment and the letter O used to designate the smallest. The electrophoretic separation of the restriction fragments is described and shown in the aforementioned publication of Panicali et al., J. Virol. 37, 1000–1010 (1981). The F-fragment obtained in this manner from either the L- or S-variants has a molecular weight of 8.6 megadaltons. The position of the F-fragment is shown on the restriction map presented as FIG. 1 accompanying the application and a restriction map of the F-fragment is shown in FIG. 2. The restriction enzyme Hind III recognizes the nucleotide sequence -AAGCTT- and cleaves the DNA between the adjacent adenosine groups to give fragments having "sticky ends" with the sequence AGCT-. Since larger quantities of the Hind III F-fragment of vaccinia than are readily obtainable by restriction of the vaccinia genome are required for manipulation according to the present invention, the F-fragment is inserted into a plasmid cloning vector for purposes of amplification.

Namely, the vaccinia Hind III F-fragment produced in this manner is conveniently introduced into the plasmid pBR 322 which is cut only once by a number of restriction enzymes, including Hind III. The pBR 322 plasmid was first described by Bolivar et al. in Gene 2, 95–113 (1977) and is now commercially available within the United States from a number of sources.

The location of the Hind III cleavage site on the pBR 322 plasmid is indicated in FIG. 3A relative to cleavage sites of Eco RI and Bam HI, which are other restriction enzymes. If the pBR 322 plasmid is cut with Hind III and the resultant cleaved DNA is mixed with vaccinia Hind III F-fragment, and if the fragments are ligated with T$_4$ DNA ligase, as suggested in FIG. 3A, the F-fragment is incorporated into the plasmid to produce the novel plasmid pDP 3 shown schematically in FIG. 3B and having a molecular weight of approximately 11.3 megadaltons. The vaccinia Hind III F-fragment includes approximately 13 kilobasepairs in comparison with the 4.5 kilobasepairs found in the pBR 322 portion of pDP 3. T$_4$ DNA ligase is a commercially available enzyme and the conditions for its use in the manner indicated are well known in the art.

The pDP 3 plasmid is now introduced into a microorganism such as *Escherichia coli* (*E. coli*) by transformation for purposes of replicating the Hind III F-fragment for recovery of larger quantities of the F-fragment. These techniques of cleaving a plasmid to produce linear DNA having ligatable termini and then inserting exogenous DNA having complementary termini in order to produce a replicon (in this case the pBR 322 containing vaccinia Hind III F-fragment) are known in the art, as is the insertion of the replicon into a microorganism by transformation (cf. U.S. Pat. No. 4,237,224).

Unmodified pBR 322 plasmid confers ampicillin resistance (Amp$^R$) and tetracycline resistance (Tet$^R$) to its host microorganism, in this case *E. coli*. However, since Hind III cuts the pBR 322 plasmid in the Tet$^R$ gene, the introduction of the vaccinia Hind III F-fragment destroys the Tet$^R$ gene and tetracycline resistance is lost. Hence, the *E. coli* transformants containing the pDP 3 plasmid can be distinguished from untransformed *E. coli* by the simultaneous presence of resistance to ampicillin and susceptibility to tetracycline. It is these *E. coli* transformed with pDP 3 which are grown in large quantities and from which large qantities of the pDP 3 are recovered.

The conditions under which plasmids can be amplified in *E. coli* are well known in the art, for example from the paper of Clewel, J. Bacteriol. 110, 667–676 (1972). The techniques of isolating the amplified plasmid from the *E. coli* host are also well known in the art and are described, for instance, by Clewel et al. in Proc. Natl. Acad. Sci. USA 62, 1159–1166 (1969).

In a similar fashion, the pBR 322 plasmid can be conveniently cleaved by treatment with the restriction enzyme Bam HI and a modified plasmid can be prepared by the insertion thereinto of a Bam HSV TK fragment, all as discussed in the aforementioned work of Colbere-Garapin et al., loc. cit. The modified plasmid containing the Bam HI fragment which includes the HSV TK gene can again be introduced into *E. coli* by known methods and the transformed bacteria grown for amplification of the plasmid in large quantities. The amplified Bam HSV TK-pBR 322 recombinant plasmid is subsequently cleaved with Bam HI to isolate the Bam HI fragment containing the HSV TK gene using the same prior art techniques mentioned earlier with regard to the amplification of the Hind III F-fragment of vaccinia.

To construct a recombinant plasmid having the Bam HI HSV TK fragment included within the vaccinia Hind III F-fragment, the pDP 3 plasmid is next subjected to a partial restriction with Bam HI such that only one of the two Bam HI cleavage sites within the plasmid is cleaved, i.e. either that Bam HI site within the Hind III F-fragment or the Bam HI site within the pBR 322 portion of the pDP 3 plasmid, as shown in FIG. 3B. The cleaved, now-linear, DNA is then combined with purified Bam HSV TK fragment. The linear segments are combined and ligated by treatment with $T_4$ DNA ligase, again using techniques known in the art.

The combination of the Bam HSV TK fragment with the cleaved pDP 3 plasmid is a random or statistical event leading to the possible production of numerous species formed by various combinations of the fragments present in the mixture, all of which have identical "sticky ends". Thus, one possibility is the simple rejoining of the Bam HI cleaved ends of the pDP 3 plasmid to reform the circular plasmid. Another possibility is the joinder of two or more Bam HSV TK fragments in either of two orientations. Further, the BamHSV TK fragment (or a multiple thereof) may be combined with the linear DNA of a pDP 3 plasmid which has been cleaved at the Bam HI site within the pBR 322 portion, again in either of two orientations, or one or more Bam HSV TK fragments may be combined, again in either of two orientations, with linear pDP 3 DNA which has been cleaved at the Bam HI site within the vaccinia Hind III F-fragment portion of the pDP 3 plasmid.

To permit the identification and separation of these various possibilities, the products of ligation are inserted into a unicellular microorganism such as *E. coli* by techniques like those described earlier and known in the art. The *E. coli* thus treated are then grown on a medium containing ampicillin. Those bacteria which contain any plasmid are ampicillin resistant beause all such plasmids contain that gene of pBR 322 which confers ampicillin resistance. Hence, all surviving bacteria are transformants which are then screened further to determine the presence or absence of the Bam HSV TK fragment possibly present.

To accomplish this, those bacteria containing any TK gene are identified by hybridization with radio-labelled TK DNA. If the TK gene is present in the bacterium, the radio-labelled TK DNA will hybridize with that portion of the plasmid present in the bacterium. Since the hybrid is radioactive, the colonies containing TK within their plasmids can be determined by means of autoradiography. The bacteria containing TK can in turn be grown. Finally, then, bacteria containing plasmids having the TK incorporated within the pBR 322 portion can be identified and separated from those having the TK fragment in the vaccinia Hind III F-fragment by analysis with restriction endonucleases.

More in detail, the bacteria surviving growth on nutrient agar plates containing ampicillin are partially transferred to a nitrocellulose filter by contact of the filter with the plate. The bacteria remaining on the plate are regrown and the bacteria which have been transferred to the nitrocellulose filter to create a replica of the original plate are next treated to denature their DNA. Denaturation is effected, for example, by treatment of the transferred bacteria with sodium hydroxide, followed by neutralization and washing. Subsequently, the now-denatured DNA present on the nitrocellulose filter is hybridized by treatment with HSV Bam TK containing radioactive $^{32}P$. The nitrocellulose filter so teated is next exposed to X-ray film which darkens in those portions in which hybridization with the radio-labelled Bam HSV TK has taken place. The exposed darkened X-ray film is next compared with the original plate and those colonies growing on the original plate corresponding to the colonies causing darkening of the X-ray film are identified as those containing a plasmid in which Bam HSV TK is present.

Finally, to discriminate between those bacteria containing a plasmid in which the Bam HSV TK gene has been incorporated within the pBR 322 portion of the plasmid from those wherein Bam HSV TK is present in the F-fragment of the plasmid, small cultures of the bacteria are grown and the plasmids are isolated therefrom by a mini-lysis technique known in the art and described in the paper of Holmes et al., Anal. Bioch. 114 193–197 (1981). The plasmids are next digested with the restriction enzyme Hind III which cleaves the circular plasmid at the two points of original joinder of the F-fragment with the pBR 322 DNA chain. The molecular weight of the digestion product is next determined by electrophoresis on agarose gels, with the distance of migration in the gels being a measure of the molecular weight.

If the Bam HSV TK fragment or a multiple thereof is found in the F-segment of the digested plasmid, the gel will show the presence of the pBR 322 fragment plus a second fragment having a molecular weight greater than that of the F-fragment by the molecular weight of the Bam HSV TK DNA segment or segments included therein. Conversely, if the Bam HSV TK is present in the pBR 322, electrophoresis will show the presence of an F-fragment of the usual molecular weight plus a further fragment larger than pBR 322 by the molecular weight of the Bam HSV TK fragment or fragments present therein. Those bacteria in which modification with Bam HSV TK has occurred in the pBR 322 portion of the plasmid are discarded: the remaining bacteria have been modified in the F-fragment portion of the plasmid therein. It is these plasmids which are used for incorporation of the Bam HSV TK fragment into vaccinia.

As mentioned earlier, the combination of the DNA fragments to regenerate a plasmid is a random event according to which a number of which different plasmid structures having Bam HSV TK in the F-fragment can result.

To determine the orientation of the Bam HSV TK fragment within the F-fragment, as well as the number of such Bam HSV TK fragments possibly present, the plasmids are recovered from each of those bacterial colonies which are known to have an Bam HSV TK fragment present in the F-fragment of the plasmid. The mini-lysis technique mentioned earlier herein is used for this purpose. The plasmids are then again subjected to restriction analysis, this time using the commercially available restriction enzyme Sst I. Since each Bam HSV TK fragment has an Sst I restriction site therein, and since the F-fragment of vaccinia similarly has a single Sst I restriction site therein (cf. the representation of these fragments in FIGS. 3B and 3A respectively), different numbers of fragments of differing molecular weights can be detected by electrophoresis on agarose gels, the number and molecular weight of the segments being dependent on the orientation of the Bam HSV TK fragment within the F-fragment and the number of such Bam TK fragments present. Orientation of the Bam TK fragment within the F-fragment can be detected because of the asymmetry of the Bam HSV TK fragment with respect to the Sst I site therein (cf. FIG. 3B).

For instance, in the particular experiments under discussion, six bacterial colonies each having one or more Bam HSV TK fragments present in the F-fragment of the plasmid were found among the E. coli transformants. After restriction analysis of the plasmids in these bacteria along the lines discussed above, two of the recombinant plasmids were chosen for further study because the direction of orientation of the Bam HSV TK fragment within the F-fragment was in opposite directions.

At this point, the reader is reminded that the introduction of the HSV TK gene into the F-fragment of vaccinia, as discussed in detail above, is merely exemplary of one of many possible means of modifying the vaccinia genome to produce desirable vaccinia mutants. Thus, the introduction of the same exogenous gene into another portion of the vaccinia genome, or the introduction of different genetic material into the vaccinia F-fragment or into some other fragment, all may require modification of the exemplary scheme, discussed above, for the identification of recombinant organisms.

For instance, digestion of the vaccinia L-variant within Ava I yields a fragment, H, entirely with the region deleted from the S-variant (cf. FIG. 6A and the discussion thereof infra). This H-fragment contains Bam HI sites permitting the introduction thereinto of the HSV TK gene. The same scheme for identifying F-fragment-HSV TK recombinants can be used for identifying such H-fragment recombinants also.

Indeed, schemes for the construction and identification of F-fragment-HSV TK recombinants, alternative to that disclosed in detail above by way of illustration, do exist. For instance, the Bam HI site in pBR 322 can be removed by cleavage of the plasmid with Bam HI and treatment with DNA polymerase I to "fill in" the "sticky ends". This product is then cut with Hind III and the linear fragment is treated with alkaline phosphatase to prevent recircularization of the plasmid upon ligation. However, foreign DNA, and particularly the vaccinia Hind III F-fragment, can be ligated to the treated pBR 322 and the resulting plasmid will recircularize. Now, treatment with Bam HI effects cleavage of the plasmid only within the vaccinia F-fragment portion thereof. Subsequent treatment of the cleavage product with alkaline phosphatase and ligation with the Bam HI HSV TK fragment will produce recombinants with high efficiency so that the recombinants can be screened by restriction endonuclease cleavage and gel electrophoresis. This technique eliminates the time-consuming steps of discriminating between recombinants having HSV TK in the pBR 322 portion or in the F-fragment and colony hybridization.

Returning now to further discussion of the plasmids produced in the exemplary mutation of vaccinia by the introduction of HSV TK into the vaccinia F-fragment, the two recombinant plasmids chosen for further study are shown in FIG. 3C, where they are identified as a first novel plasmid, pDP 132, incorporating one Bam HSV TK fragment within the vaccinia Hind III F-portion, and a second novel plasmid, pDP 137, in which two Bam HSV TK fragments joined "head to tail" have been incorporated. The single fragment of Bam HSV TK has been incorporated within pDP 132 in the opposite sense in which two Bam TK fragments have been included in tandem in pDP 137. Namely, the region of the TK gene within the Bam HI fragment which codes for the 5'-end of mRNA produced by the gene is located between the Sst I cleavage site and the nearer of the two Bam HI sites thereto (again cf. FIG. 3B). The direction of transcription of the HSV TK gene on the Bam TK fragment proceeds from the 5'-end to the 3'-end and will be in a clockise direction in pDP 132 as shown in FIG. 3C. [cf. Smiley et al., Virology 102, 83–93 (1980)]. Conversely, since the Bam TK fragments included in tandem in pDP 137 have been incorporated in the reverse sense, transcription of the HSV TK genes contained therein will be in the opposite direction, namely in a counter-clockwise direction. The direction of inclusion of the Bam HSV TK fragment within the vaccinia Hind III F-fragment may be of importance in case promotion of transcription of the HSV TK gene is initiated by a promoter site within the F-fragment itself. However, HSV promoter sites do exist within the Bam HSV TK fragment itself, so that transcription of the HSV TK gene may occur no matter in which direction the Bam HSV TK fragment and HSV TK gene have been incorporated within the vaccinia Hind III F-fragment.

Those E. coli transformants containing pDP 132 or pDP 137 are next grown to produce large amounts of the plasmids for further processing. When a sufficient amount of the plasmid DNA has been isolated, restriction with Hind III yields a modified vaccinia Hind III F-fragment having the HSV TK gene therein. This modified Hind III F-fragment is now introduced into vaccinia virus by novel methods, described below in greater detail, in order to produce an infectious entity.

To review the prior art, at present the vector principally used for introducing exogenous DNA into eukaryotic cells is SV40. The DNA of SV40 is circular and can be treated much like a plasmid. That is, the circular DNA is cleaved with a restriction enzyme, combined with exogenous DNA, and ligated. The modified DNA can be introduced into eukaryotic cells, for instance animal cells, by standard techniques [cf. Hamer et al., Nature 281, 35–40 (1979)]. The DNA is infectious and will replicate in the nucleus of the cell producing viable mutated viruses. In contrast, vaccinia replicates within the cytoplasm of a eukaryotic cell. The purified DNA of this virus is not infectious and cannot be used per se to produce vaccinia mutants in a cell in the same manner as SV40. Rather, novel techniques involving the mutation of wild type vaccinia with foreign DNA in vivo within a cell must be employed.

An unpublished paper of the applicants, together with Eileen Nakano (Nakano et al., Proc. Nat'l Acad. Sci. USA 79, 1982, 1593–1596), reports a demonstration of marker rescue in vaccinia virus. According to these experiments, that portion of the L-variant DNA which is normally absent from the S-variant can be reintroduced into the S-variant ("rescued") under appropriate conditions. Namely, eukaryotic cells are treated with live infectious S-variant vaccinia virus together with non-infectious restriction fragments of the DNA of the L-variant, representing DNA "foreign" to the S-variant, of a particular structure. Namely, that portion of the L-variant DNA which is to be rescued must be present within a DNA chain having portions co-linear with the DNA chain of the S-fragment into which it is to be introduced. That is, the "foreign" DNA to be introduced into the S-variant has, at both ends of the DNA chain, a region of DNA which is homologous with corresponding sequences in the S-variant. These homologous sequences can be viewed as "arms" attached to the region of L-variant DNA which is to be rescued by the S-variant.

The mechanism of this recombination is complex and has not yet been accomplished in vitro. Apparently, the recombination of the L-DNA into the S-variant involves homologous base pairing in segments surrounding the area deleted from the S-variant. Most likely, cross-overs from one strand of DNA to another result in an in vivo recombination of the DNA to rescue the deleted portion.

This technique of in vivo recombination can be used to introduce foreign DNA other than vaccinia DNA into either the S- or the L-variant of vaccinia. Thus, the modified Hind III F-fragment incorporating the Bam HSV TK fragment therein as DNA "foreign" to vaccinia can be introduced into vaccinia by treating eukaryotic cells with the modified F-fragment together with infectious L- and/or infectious S-variants of vaccinia virus. In this instance, the portions of the F-fragment flanking the Bam HSV TK fragment function as the "arms" mentioned earlier, comprising DNA homologous with DNA present in the L- or S-variant into which the modified F-fragment is to be introduced. Again, by in vivo processes within the cell, the mechanisms of which are not known in detail, the HSV TK-modified F-fragment is incorporated into the vaccinia variants in the cell and is then capable of replication and expression under vaccinia control.

This in vivo recombination technique is broadly applicable to the introduction of still other "foreign" DNA into vaccinia, providing a pathway by which the genome of vaccinia can be modified to incorporate a wide variety of foreign genetic material thereinto, whether such foreign DNA be derived from vaccinia itself, be synthetic, or be derived from organisms other than vaccinia.

A wide variety of cells can be used as the host cells in which the in vivo recombination described above takes place. The recombination, however, occurs with differing efficiency depending on the cell employed. Of the cells investigated to date, baby Syrian hamster kidney cells [BHK-21 (Clone 13) (ATCC No. CCL10)] have proved most efficient for the recombination procedure. However, other cells including CV-1 (ATCC No. CCL70), a green monkey kidney cell line, and human (line 143) TK-cells, a 5'-BUdR resistant mutant derived from human cell line R970-5, have also been infected in this manner to generate vaccinia mutants.

These cells are suitably treated with vaccinia and the foreign DNA to be incorporated into the vaccinia while, for convenience, the cells are in the form of a monolayer. For purposes of in vivo recombination, the cells may be infected with vaccinia followed by treatment with the foreign DNA to be incorporated thereinto, or may first be contacted with the foreign DNA followed by infection with vaccinia. As a third alternative, the vaccinia and foreign DNA may be simultaneously present at the time the cells are treated.

The viruses are suitably contacted with the cell monolayer while present in a conventional liquid medium, such as phosphate buffered saline, Hepes buffered saline, Eagle's Special medium (with or without serum addition), etc., which is compatible with these cells and the viruses.

The foreign DNA is conveniently used to treat these cells while in the form of a calcium phosphate precipitate. Such techniques for introducing DNA into cells have been described in the prior art by Graham et al., Virology 52, 456–467 (1973). Modifications of the technique have been discussed by Stow et al., J. Gen. Virol. 33, 447–458 (1976) and Wigler et al., Proc. Natl. Acad. Sci. USA 76, 1373–1376 (1979). The treatments taught in these papers conveniently proceed at room temperature, but temperature conditions can be varied within limits preserving cell viability, as can the time for which the cells are treated with the virus and/or foreign DNA precipitate, with various efficiencies of the in vivo recombination. The concentration of the infecting vaccinia virus and the amount of foreign DNA precipitate employed will also affect the rate or degree of recombination. Other factors such as atmosphere and the like are all chosen with a view to preserving cell viability. Otherwise, as long as the three necessary components (cell, virus, and DNA) are present, in vivo recombination will proceed at least to some extent. Optimization of the conditions in a particular case is well within the capabilities of one skilled in the microbiological arts.

Following this recombination step, those vaccinia viruses which have been mutated by in vivo recombination must be identified and separated from unmodified vaccinia virus.

Vaccinia viruses mutated by in vivo recombination of foreign DNA thereinto can be separated from unmodified vaccinia virus by at least two methods which are independent of the nature of the foreign DNA or the ability of the mutant to express any gene which may be present in the foreign DNA. Thus, first, the foreign DNA in the mutant genome can be detected by restriction analysis of the genome to detect the presence of an extra piece of DNA in the mutated organism. In this method, individual viruses isolated from purified plaques are grown and the DNA is extracted therefrom and subjected to restriction analysis using appropriate restriction enzymes. Again, by detecting the number and molecular weight of the fragments determined, the structure of the genome prior to restriction can be deduced. However, because of the necessity of growing purified plaques, the number of analyses which must be made, and the possibility that none of the plaques grown and analyzed will contain a mutant, this technique is laborious, time consuming and uncertain.

Further, the presence of foreign DNA in vaccinia virus can be determined using a modification of the technique taught by Villarreal et al. in Science 196, 183–185 (1977). Infectious virus is transferred from viral plaques present on an infected cell monolayer to a nitrocellulose filter. Conveniently, a mirror-image replica of the transferred virus present on the nitrocellulose filters is made by contacting a second such filter with that side of the first nitrocellulose filter to which the viruses have been transferred. A portion of the viruses present on the first filter is transferred to the second filter. One or the other of the filters, generally the first filter, is now used for hybridization. The remaining filter is reserved for recovery of recombinant virus therefrom once the locus of the recombinant virus has been detected using the hybridization technique practiced on the companion, mirror-image filter.

For purposes of hybridization, the viruses present on the nitrocellulose filter are denatured with sodium hydroxide in a manner known per se. The denatured genetic material is now hybridized with a radio-labelled counterpart of the gene whose presence is sought to be determined. For example, to detect the possible presence of vaccinia mutants containing the Bam HSV TK fragment, the corresponding radio-labelled Bam HSV TK fragmet containing $^{32}P$ is employed, much in the same manner as discussed earlier herein with respect to the detection of plasmids modified by the presence of this fragment. Non-hybridized DNA is washed from the nitrocellulose filter and the remaining hybridized DNA, which is radioactive, is located by autoradiography, i.e. by contacting the filter with X-ray film. Once the mutated viruses are identified, the corresponding virus plaques present on the second filter, containing a mirror image of the viruses transferred to the first filter, are located and grown for purposes of replicating the mutated viruses.

The two methods described above involve an analysis of the genotype of the organism involved and, as mentioned earlier, can be used whether or not any gene present within the foreign DNA incorporated into the vaccinia virus is expressed. However, if the foreign DNA is expressed, then phenotypic analysis can be employed for the detection of mutants. For example, if the gene is expressed by the production of a protein to which an antibody exists, the mutants can be detected by a method employing the formation of antigen-antibody complexes. See Bieberfeld et al. J. Immunol. Methods 6, 249-259 (1975). That is, plaques of the viruses including the suspected mutants are treated with the antibody to the protein which is produced by the mutant vaccinia genotype. Excess antibody is washed from the plaques, which are then treated with protein A labelled with $^{125}I$. Protein A has the ability of binding to the heavy chains of antibodies, and hence will specifically label the antigen-antibody complexes remaining on the cell monolayer. After excess radioactive protein A is removed, the monolayers are again picked up by plaque lifts onto nitrocellulose filters and are subjected to autoradiography to detect the presence of the radio-labelled immune complexes. In this way, the mutated vaccinia viruses producing the antigenic protein can be identified.

In the specific instance in which the foreign DNA includes the HSV TK gene, once it is known that the mutated vaccinia virus expresses the HSV TK gene therein, a much simpler and elegant means for detecting the presence of the gene exists. Indeed, the ease of discrimination between vaccinia mutants containing the HSV TK gene and unmodified vaccinia free of this gene provides a powerful tool for discriminating between vaccinia virus mutants containing other exogenous genes either present alone in the vaccinia genome or present therein in combination with the HSV TK gene. These methods are described more in detail later herein.

Since eukaryotic cells have their own TK gene and vaccinia virus similarly has its own TK gene (utilized, as noted above, for the incorporation of thymidine into DNA), the presence and expression of these genes must be in some way distinguished from the presence and expression of the HSV TK gene in vaccinia mutants of the type under discussion. To do this, use is made of the fact that the HSV TK gene will phosphorylate halogenated deoxycytidine, specifically iododeoxycytidine (IDC), a nucleoside, but neither the TK gene of vaccinia nor the TK gene of cells will effect such a phosphorylation. When IDC is incorporated into the DNA of a cell it becomes insoluble. Non-incorporated IDC, on the other hand, is readily washed out from cell cultures with an aqueous medium such as physiologic buffer. Use is made of these facts as follows to detect the expression of the HSV TK gene in vaccinia mutants.

Namely, cell monolayers are infected with mutated virus under conditions promoting plaque formation, i.e. those promoting cell growth and virus replication. When the cells are infected, they are then treated with commercially available radio-labelled IDC (IDC*), labelling being easily effected with $^{125}I$. If the cells are infected with a virus containing the HSV TK gene, and if the HSV TK gene present therein is expressed, the cell will incorporate IDC* into its DNA. If the cell monolayers are now washed with a physiologic buffer, non-incorporated IDC* will wash out. If the cell monolayers are next transferred to a nitrocellulose filter and exposed to X-ray film, darkening of the film indicates the presence of IDC* in the plaques and demonstrates the expression of the HSV TK gene by the vaccinia mutants.

Using the aforementioned genotypic and phenotypic analyses, the applicants have identified two vaccinia mutants denominated VP-1 and VP-2. VP-1 (ATCC No. VR 2032) is a recombinant vaccinia virus derived from vaccinia S-variant modified by in vivo recombination with the plasmid pDP 132. VP-2 (ATCC No. VR 2030) is an S-variant vaccinia virus modified by recombination with pDP 137.

FIG. 4A is a Hind III restriction map of the vaccinia genome showing the site of the HSV TK gene insertion. FIGS. 4B and 4C magnify the Hind III F-fragment respectively contained in VP-1 and VP-2 to show the orientation of the Bam HI HSV TK fragment therein. Attention is called to the fact that the in vivo recombination of pDP 137 with the S-variant (i.e. VP-2) effects deletion of one of the Bam HI HSV TK fragments present in tandem in the starting plasmid.

As mentioned earlier, the fact that the HSV TK gene is expressed can be used for a rapid and easy detection and identification of mutants which contain or are free of HSV TK gene or of a foreign gene present alone or in combination with the HSV gene. The test and its bases are described immediately below.

The applicants have isolated, in biologically pure form, a vaccinia mutant, an S-variant in particular, which is free of any naturally-occurring functional TK gene, denominated VTK−79 (ATTC No. VR 2031). Normally, the S- and L-variants discussed earlier herein have a TK gene in the Hind III fragment J thereof. If this mutant, free of vaccinia TK gene activity, is used for the production of further mutated organisms containing the HSV TK gene, incorporated into the vaccinia mutant by the techniques described earlier herein, the HSV TK gene present in such resultant mutants will be the only functional TK gene present in the virus. The presence or absence of such an HSV TK gene can be immediately detected by growing cells infected with the viruses on one of several selective media.

Namely, one such selective medium contains bromodeoxyuridine (BUdR), a nucleoside analogous to thymidine, but highly mutagenic and poisonous to organisms such as a cell or virus when present in DNA contained therein. Such a medium is known from Kit et al., Exp. Cell Res. 31, 297-312 (1963). Other selective media are the hypoxanthine/aminopterin/thymidine (HAT) medium of Littlefield, Proc. Natl. Acad. Sci. USA 50, 568-573 (1963) and variants thereof such as MTAGG, described by Davis et al., J. Virol. 13, 140-145 (1974) or the further variant of MTAGG described by Campione-Piccardo et al. in J. Virol. 31, 281-287 (1979). All these media selectively discriminate between organisms containing and expressing a TK gene and those which do not contain or express any TK gene. The selectivity of the media is based on the following phenomena.

There are two metabolic pathways for the phosphorylation of thymidine. The primary metabolic pathway does not rely upon thymidine kinase and, while it synthesizes phosphorylated thymidine by intermediate mechanisms, it will not phosphorylate BUdR or directly phosphorylate thymidine. The secondary metabolic pathway does involve the activity of thymidine kinase and will result in the phosphorylation of both thymidine and its analog, BUdR. Since BUdR is a poisonous highly mutagenic substance, the presence of TK, such as the HSV TK under discussion, in an organism will result in the phosphorylation of BUdR and its incorporation into the DNA of the growing organism, resulting in its death. On the other hand, if the TK gene is absent or not expressed, and the primary metabolic pathway which then is followed results in the synthesis of phosphorylated thymidine, but not in the phosphorylation of BUdR, the metabolizing organism will survive in the presence of BUdR since this substance is not incorporated into its DNA.

The growth behaviors discussed above are summarized in FIG. 5 of the accompanying drawings tabulating the growth behavior by organisms expressing TK (TK+) and organisms free of or not expressing the TK gene (TK−) on a normal medium, on a selective medium such as HAT which blocks the primary metabolic pathway not using TK, and on a medium containing BUdR. TK+ and TK− organisms will both grow on a normal growth medium by employing the primary metabolic pathway not requiring TK. On a selective medium such as HAT which blocks the primary metabolic pathway not relying on TK, the TK+ organism will nevertheless grow because the enzyme accomplishes the phosphorylation necessary for incorporation of thymidine into DNA. On the other hand, the TK− organisms will not survive. In contrast, if the organisms are grown on a medium containing BUdR, the TK+ variants will die since TK phosphorylates BUdR and this poisonous material is incorporated in the DNA. In contrast, since BUdR is not phosphorylated by the primary metabolic pathway, the TK− variant will grow since BUdR is not incorporated into the DNA.

Thus, if a vaccinia virus free of vaccinia TK, such as VTK−79, is used as the vaccinia virus into which the HSV TK gene is inserted by the techniques of the present invention, the presence and expression, or the absence, of the HSV TK gene therein can be readily determined by simply growing the recombinants on a selective medium such as HAT. Those viruses which are mutated will survive since they use the HSV TK to synthesize DNA.

The applicants have indeed prepared several mutants of vaccinia virus free of vaccinia TK. These have been denominated VP-3 (ATCC No. VR 2036), a recombinant of VTK−79 and pDP 132, and VP-4 (ATCC No. VR 2033), a recombinant of VTK−79 and pDP 137. The latter expresses the HSV gene and can readily be identified using the selective media mentioned above.

Two additional recombinant viruses, denominated VP-5 (ATCC No. VR 2028), and VP-6 (ATCC No. VR 2029), are respectively recombinants of pDP 132 and pDP 137 with VTK−11 (ATCC No. VR 2027), a known L-variant of vaccinia which does not express the vaccinia TK gene. Thus, DNA can be introduced in excess of the maximum vaccinia genome length.

The techniques of the present invention can be used to introduce the HSV TK gene into various portions of the vaccinia genome for purposes of identifying non-essential portions of the genome. That is, if the HSV TK gene can be inserted into the vaccinia genome, as it is in the Hind III F-fragment thereof, the region of the genome into which it has been introduced is evidently non-essential. Each non-essential site within the genome is a likely candidate for the insertion of exogenous genes so that the methods of the present invention are useful in mapping such non-essential sites in the vaccinia genome.

Further, if the HSV TK gene is coupled with another exogenous gene and the resultant combined DNA material is put into a vaccinia virus free of vaccinia TK gene, such as VTK−79, recombinants which are formed and which contain the foreign gene will express the HSV TK gene and can be readily separated from the TK− variants by the screening technique described immediately above.

A further embodiment of the invention involves the preparation of a vaccinia Hind III F-fragment containing an exogenous gene therein and the treatment of cells with the fragment together with a vaccinia mutant not expressing the vaccinia TK gene but having the HSV TK gene incorporated therein by in vivo recombination according to the techniques of the present invention. As with the marker rescue mentioned earlier herein, and the in vivo techniques employed to incorporate the TK-modified Hind III F-fragment into vaccinia, crossover and recombination can occur to produce a further mutant in which the HSV TK modified F-fragment is replaced by an F-fragment containing another exogenous gene. The resulting vaccinia mutant, in which the HSV TK F-fragment has been replaced by an F-fragment containing the exogenous gene, will be totally free of TK, whereas the non-mutated parent virus predominantly present will still be HSV TK+. Similarly a foreign gene may be inserted into the HSV TK gene present in such a vaccinia mutant, disrupting the integrity of the gene rendering the recombinant organism TK− in comparison with the non-mutated TK+ parent. In both instances, an immediate discrimination can be made between those vaccinia mutants containing the foreign gene and those which are free of any TK by growth on BUdR and/or a special medium such as HAT.

FIGS. 7A-C can best be understood in conjunction with FIGS. 3A-C. Thus, it will be seen from FIG. 3B that plasmid pDP, prior to the incorporation of any additional DNA therein, has a molecular weight of 11.3 megadaltons (md). When further DNA is incorporated therein, such as the herpes Bam TK fragment shown in FIG. 3B, to produce plasmids pDP 132 and pDP 137, the latter plasmids have an increased molecular weight of, respectively, 13.6 and 15.9 md. Since these molecular weights are approximately at the upper limit of replication for the plasmid, it has proved desirable to create a plasmid containing the vaccinia Hind III F-fragment, but which plasmid is of a lower molecular weight than pDP 3 shown in FIG. 3B. A method for creating such a lower molecular weight plasmid is shown in FIGS. 7A-C.

More in particular, FIG. 7A shows plasmid pDP 3 containing the Hind III F-fragment of vaccinia of molecular weight 8.6 megadaltons. As shown in the Figure, the plasmid contains three sites susceptible to cleavage by the restriction enzyme Pst I. Two of these sites are within the F-fragment portion of the plasmid, while the third is within that portion of the plasmid which is derived from parent plasmid pBR 322. As further shown in FIG. 7A, when plasmid pDP 3 is cleaved with Pst I, three fragments are obtained. The fragment which is solely a portion of the vaccinia Hind III F-fragment has a molecular weight of 3.7 md. There are also two other fragments each combining portions of the parent pBR 322 and vaccinia Hind III F-fragment.

The largest, "pure" F-subfragment, can be easily isolated. As shown in FIG. 7B, the fragment can then be introduced into pBR 322 at a Pst I site therein after cleavage of the pBR 322 plasmid with Pst I. The joinder of the parent fragments with $T_4$ DNA ligase produces the new plasmid pDP 120, shown in FIG. 7C, which has a molecular weight of only 6.4 md. The lower molecular weight of the pDP 120 plasmid, in comparison with pDP 3, permits the introduction thereinto of longer DNA sequences without approaching the upper limit of replication as do plasmids pDP 132 and pDP 137 shown in FIG. 3C.

Again, a better understanding of FIGS. 8A–D will be had by referring to FIGS. 3A–C. More in particular, FIGS. 3B and 3C show the incorporation of a herpes Bam TK fragment into plasmid pDP 3 to form plasmids pDP 132 and 137. As explained more in detail in Example X of the application, this herpes Bam TK fragment is introduced into vaccinia virus by an in vivo recombination technique involving simultaneous treatment of suitable cells with vaccinia virus and Hind III-treated pDP 132 or pDP 137. It will be evident from an inspection of FIG. 3C that treatment of the aforementioned plasmids with Hind III will excise that portion of the plasmids originally derived from plasmid pBR 322, since the herpes Bam TK fragment to be incorporated into the vaccinia virus by in vivo recombination was present in a vaccinia Hind III F-fragment joined with the pBR 322 segment at a Hind III site. Thus, the herpes Bam TK gene is incorporated into vaccinia without the pBR 322 DNA sequence.

However, because of the numerous restrictions sites available in the pBR 322 plasmid, for example including Eco RI, Hind III, Bam HI, Pst I, etc., the plasmid is particularly advantageous for the introduction of DNA sequences thereinto. Hence, it would be desirable to be able to introduce pBR 322 into a vector such as vaccinia virus.

FIGS. 8A–D show the development of two plasmids by means of which the versatile DNA sequence of pBR 322 can be incorporated into vaccinia virus by in vivo recombination and, particularly, the production of two vaccinia mutants, VP 7 and VP 8, containing the pBR 322 DNA sequence.

More in particular, FIG. 8A shows the vaccinia Hind III F-fragment also shown in FIG. 3A of the drawings. The linear segment can be self-ligated to form a circular F-fragment as also shown in FIG. 8A. The joined Hind III termini are indicated on both the linear and circular fragment as "a" and "d", respectively. The termini on either side of a Bam HI site are also shown in FIG. 8A as "c" and "b".

As particularly shown in FIG. 8B, this circularized F-fragment can be treated with Bam HI to produce a linear DNA sequence in which the Bam HI termini "b" and "c" are shown with respect to the Hind III termini "a" and "d". This linear sequence will be referred to as an "inverted F-fragment".

If, as further shown in FIG. 8B, Bam HI-treated pBR 322 and the linear inverted F-fragment sequence of FIG. 8B are combined with $T_4$ DNA ligase, two plasmids are produced, depending on the relative alignment of the inverted F-fragment and the parent pBR 322 sequence. These two plasmids are shown in FIG. 8C as pDP 301 B and pDP 301 A, each of which has the same molecular weight of 11.3 md.

The incorporation of plasmids pDP 301 A and 301 B into vaccinia by in vivo recombination is shown in FIG. 8D. Namely, each of these plasmids was incorporated by in vivo recombination into vaccinia virus VTK$^-$79, respectively to produce vaccinia mutants VP 7 (ATCC No. VR 2042) and VP 8 (ATCC No. VR 2053). As shown in this Figure, for this purpose the pDP 301 plasmids are each cleaved with Sst I to produce linear DNA sequences the termini of which are homologous with a corresponding DNA sequence present in the F-portion of the vaccinia virus genone. Simultaneous treatment of cells with the Sst I-treated plasmids and vaccinia virus results in in vivo recombination with incorporation of the pBR 322 DNA sequence into the virus genome.

The advantage of the presence of the pBR 322 sequence in the vaccinia genome of VP 7 and VP 8 is that in vivo recombination can be readily effected using these variants and pBR 322 sequences modified to have a variety of foreign DNA sequences therein. In this instance, it is the homologous base pairs of pBR 322 in the vaccinia genome and in the modified pBR 322 DNA sequence to be introduced which facilitate crossover and recombination, as is illustrated hereinafter with respect to the construction of further new vaccinia virus mutants identified as VP 10, VP 13, VP 14, and VP 16.

FIGS. 9 and 10 concern the insertion of an influenza gene into vaccinia to provide two further vaccinia mutants, VP 9 and VP 10.

The influenza genome consists of eight separate pieces of RNA each of which codes for at least one different protein. One of the principal immunogenic proteins is the hemagglutinin protein and because of this the HA gene was chosen for insertion into vaccinia. The genome of the influenza virus contains genes in an RNA sequence and, for incorporation into a plasmid, they must be converted into a DNA copy, identified as cDNA. As known in the art, the cDNA copy of the HA RNA genome is made using reverse transcriptase, all as described by Bacz et al. in Nucleic Acids Research 8, 5845–5858 (1980).

The influenza virus exists in a number of variants, classified according to the nature of the HA gene and another of the eight genes, namely that coding for neuraminidase. Within the influenza virus family, there are three main types of the HA serotype, designated H1-H3.

In the construction of vaccinia virus mutant VP 9 and 10, the influenza virus employed was A/PR/8/34, which contains an H1 HA gene.

FIG. 9A shows two circular plasmids, pJZ 102 A and pJZ 102 B. The plasmids were prepared by incorporating a cDNA copy of the influenza hemagglutinin (HA) gene into pBR 322 at the Hind III site. The A and B plasmid variants differ in the orientation of the HA gene therein, as has been indicated in FIG. 9A by reference to an initiation codon contained within the HA gene and located within the gene by its proximity to an Ava I site within the gene. The relative positions of the Ava I site and the initiation codon in the pJZ 102 A and B variants are indicated in FIG. 9A.

If plasmid pJZ 102 A is treated with Bam HI and T4 DNA ligase in the presence of an "inverted" F-fragment of vaccinia virus (the latter shown in FIG. 8B), the result is a further plasmid shown in FIG. 9B as pJZ 102 A/F in which the pJZ 102 A parent plasmid is combined with the vaccinia F-fragment.

As further shown in FIG. 9B, if the pJZ 102 A/F plasmid shown in FIG. 9B is incorporated into the VTK−79 strain of vaccinia virus by in vivo recombination, a vaccinia mutant, VP 9 (ATCC VR No. 2043), is produced, which mutant contains and expresses the influenza hemagglutinin antigen (HA) gene and can be used, as hereinafter described, to promote the production of antibodies to the antigen in a mammal.

FIG. 9C is a map of that portion of the genome of VP 9 containing the pJZ 102 A/F DNA sequence and the HA gene therein.

FIGS. 10A-C show the construction of a second vaccinia mutant containing the influenza hemagglutinin (HA) gene, which vaccinia mutant is designated herein as VP 10 (ATCC No. VR 2044).

More in particular, the VP10 mutant is constructed by in vivo recombination of DNA from plasmid pJZ 102 B (cf. FIG. 9A) with the pBR 322 DNA sequence found in vaccinia mutant VP 7, the production of which mutant from plasmid pDP 301A is shown in FIGS. 8C and 8D.

Thus, FIG. 10A is a linear DNA map of pJZ 102B after treatment of that circular plasmid with Bam HI. Again, the initiation codon within the HA gene is indicated with reference to an Ava I site within the gene which is, in turn, contained within the DNA sequence of plasmid pBR 322. FIG. 10B shows a portion of the genome found within vaccinia mutant VP 7 as the result of the incorporation of plasmid pDP 301A into VTK−79 by in vivo recombination. More in particular, FIG. 10B shows the presence of the pBR 322 genome surrounded on each side by portions of the F-fragment of vaccinia virus, the presence of which F "arms" permitted the incorporation of the pBR 322 DNA sequence into the vaccinia genome in the first place.

Reference has been made earlier in the specification to using in vivo recombination to render an HSV TK+ vaccinia virus HSV TK−. This involves replacing the HSV TK gene, present in such a virus, with an HSV TK gene containing a foreign gene therein rendering the HSV gene TK−. The work under discussion illustrates such a technique using other DNA, specifically pBR 322 DNA, which also is exogenous to vaccinia. That is, recombination will occur with vaccinia so long as there are homologous sequences, in the transfecting (donor) DNA and in the infecting virus, flanking the foreign gene to be inserted, whether such sequences are or are not endogenous vaccinia sequences. Still other DNA sequences can be inserted into vaccinia and subsequently utilized for in vivo recombination in a similar fashion.

Because of the presence of homologous base pairs in the pBR 322 portions of pJZ 102B (shown in FIG. 10A) and the pBR 322 DNA sequence contained within the genome of VP 7 (cf. FIG. 10B), crossover can occur during in vivo recombination involving the simultaneous treatment of cells with VP 7 and pJZ 102B, with the incorporation of the HA fragment into the vaccinia genome to create the vaccinia mutant VP 10, as shown in FIG. 10C.

VP 10 illustrates that recombination in vivo can occur within the 350 base pairs between the Hind III and Bam HI sites at the right end of the pBR 322 sequences shown in FIGS. 10A-C.

To determine wether or not viruses VP 9 and VP 10 are expressing the HA gene, a series of tissue cultures was prepared. Namely, BHK cells, present in a first pair of Petri dishes, were infected with A/PR/8/34 influenza virus. CV-1 cells, present in another pair of Petri dishes were infected with VP 9 vaccinia variant, and CV-1 cells present in a third pair of Petri dishes were infected with the VP 10 vaccinia variant. After permitting the viruses to grow within the cells, the infected cells present in one of each of the three pairs of Petri dishes were treated with H1 HA antiserum: the second set of three cell cultures (one BHK and two CV-1 cultures) were treated with H3 HA antiserum. All of the cell cultures were next washed and then treated with protein A labelled with $^{125}I$. After treatment with the labelled protein A, the cell cultures are again washed and then radioautographed. If influenza antigen is being produced by the infected cells, the antigen will react with antibodies contained within the H1 HA antiserum but not the H3 HA antiserum. These complexes will not be washed from the plates and the $^{125}I$ protein A will bind with the constant portion of the heavy chains of the residual antibody in the complex if the complex is present.

It was determined that complexes were formed in the Petri dish infected with A/PR/8/34 and treated with H1 HA antiserum, as was also true of the CV-1 cells infected with VP 9. In contrast, no antigen-antibody complexes were formed in any cells infected with VP 10, nor was any complex formation detected in the cell cultures infected either with A/PR/84 or VP 9 when these cell cultures were treated with H3 HA antiserum.

From this experiment, it can be concluded, first, that the VP 10 vaccinia variant does not express the H1 HA gene at a level detectable by this assay. Conversely, the VP 9 variant does express this gene. Further, the expression VP 9 is specific to H1 HA, since there is no complex formation in the VP 9-treated cell cultures which are subsequently contacted with H3 HA antiserum.

Knowing that VP 9 expresses the H1 HA gene in vitro, it was next tested whether the VP 9 vaccinia mutant would sufficiently express the H1 HA gene to stimulate the formation of antibodies in an animal infected with this vaccinia mutant.

For this test, rabbits were infected with vaccinia virus VP 9 by intravenous injection. After 17, 25, and 41 days, blood was withdrawn from the rabbits and the serum was collected. The presence of antibodies to H1 HA within this serum was tested by a series of in vitro experiments similar to those earlier described involving the infection of cell cultures with A/PR/8/34 and VP 9. The formation of an immune complex was observed when a cell layer infected with VP 9 was treated with the rabbit antiserum. However, this test merely indicates that the rabbit produced antibodies to the vaccinia virus: it is not possible to determine whether antibodies were produced specifically to the H1 HA antigen. However, the formation of a complex between the rabbit antiserum and a BHK cell monolayer infected with A/PR/8/34 did indicate the presence, in the antiserum, of antibodies specific to the H1 HA antigen.

As a separate criterion for the production of HA antibodies, an hemagglutinin inhibition assay was performed. This test makes use of the property of HA to agglutinate red blood cells into large complexes.

To perform the assay, the rabbit antiserum was first serially diluted. Each serial dilution of the antiserum was reacted with the same fixed quantity of hemagglutinin, obtained by extracting cells infected with influenza virus. If antibodies are present in the antiserum in an amount equal to or in excess of the amount of hemagglutinin introduced into each serial dilution, the resulting mixture will inhibit the agglutination of red blood cells admixed therewith because of the presence of an excess of antibody with respect to the agglutinating agent, HA.

In the serial dilution performed (on the 45 day antiserum), all dilutions up to and including 1:320 inhibited red blood cell agglutination. This indicated the presence, in the antiserum, of H1 HA antibodies in an amount in excess of the HA antigen added thereto.

These experiments demonstrate two important facts. First, it is possible to create a vaccinia mutant according to the techniques of the present invention, which mutant when introduced into an animal model will stimulate the production, even with only primary infection, of antibody to a protein coded for by a gene within the vaccinia mutant, which gene is foreign both to vaccinia and to the animal into which it is introduced. Second, the experiments show that the production of antibodies by the animal to vaccinia itself does not interfere with the simultaneous production of antibodies to the product coded for by the foreign DNA contained within the vaccinia mutant.

The construction of plasmids pDP 250A and pDP 250B and their incorporation into VTK⁻79 to give, respectively, new vaccinia mutants VP 12 (ATCC No. VR 2046) and VP 11 (ATCC No. VR 2045) is shown in FIGS. 11A–E.

It is possible to isolate a circular DNA comprising the entire hepatitis B virus (HBV) genome. As shown in FIG. 11A, the genome is represented as comprising a region coding for the surface antigen, including a pre-surface antigen region containing an Eco RI site therein. These surface antigen regions are depicted in FIG. 11A as a "block" contained within the genome, the remaining DNA of which is represented by a zigzag line. When the genome is treated with Eco RI to cleave it, the linear DNA sequence obtained is disrupted in the pre-surface antigen portion thereof such that a portion of the pre-surface antigen region is present at each terminus of the linear DNA sequence. The two termini of the sequence, one on each side of the Eco RI site in the circular genome, are represented both in the circular genome and the linear DNA fragment respectively by a circle and square.

If the HBV DNA fragment is now incorporated into pBR 322, as shown in FIG. 11B, and that plasmid which contains two hepatitis B fragments in tandem is isolated, the known plasmid pTHBV 1, shown in FIG. 11B, is obtained. This plasmid will contain therein the reconstructed pre-surface antigen and surface antigen regions of the original hepatitis B genome, as has been pointed out by encircling these regions with dashed lines in the depiction given of plasmid pTHBV 1 in FIG. 11B. This entire construction is described by Hirschman et al, Proc. Natl. Acad. Sci. USA 77, 5507–5511 (1980).

This sAg region of pTHBV 1 can be isolated by treatment of the plasmid with the restriction enzyme Bgl II. The pBR 322 portion of the pTHBV 1 plasmid contains no Bgl II site, while each of the two HBV DNA fragments, present in tandem in the plasmid contains three Bgl II sites. Thus, pTHBV 1 contains six Bgl II sites, all in the HBV DNA, but all of which are outside the sAg region. Thus, as shown in FIGS. 11B and 11C, cleavage of pTHBV 1 with Bgl II will produce a linear DNA fragment containing the sAg region of the hepatitis B virus. [Galibert et al., Nature 281, 646–650 (1979)].

This fragment can be incorporated into the plasmid pDP 120, the production of which is earlier described in FIGS. 7A–C, although the pDP 120 plasmid contains no Bgl II site.

The recognition sequence for the enzyme Bgl II is -AGATCT- with the cleavage site being between -A and GATCT-. On the other hand, the recognition site for Bam HI is -GGATCC-, with the cleavage site being between -G and GATCC-. Thus, if DNA containing either of these recognition sites is respectively cut with Bgl II or Bam HI, in each case a -GATC- "sticky end" will be produced, which ends will be ligatable (but then no longer subject to cleavage by either Bgl II or Bam HI).

The new plasmids pDP 250 A and pDP 250 B are constructed as shown in FIGS. 11C and D by partial cleavage of pDP 120 with Bam HI and ligation of the "sticky ends" so produced with the corresponding "sticky ends" of the Bgl II fragment of the hepatitis virus genome.

As known in the art, it is possible to discourage the re-circularization of Bam HI-cleaved pDP 120 by treatment of the cleaved plasmid with alkaline phosphatase, an enzyme which removes terminal phosphoric acid groups from the 5'-cleaved ends of the linear DNA of pDP 120. Removal of the phosphoric acid groups prevents a re-circularization reaction of the pDP 120, but does not interfere with reaction of the 3'-OH termini of the linear pDP 120 DNA with the 5'-phosphate ends present on the Bgl II fragments, with subsequent circularization to produce plasmids such as pDP 250 A and pDP 250 B. Thus, the statistical probability for the creation of the latter, tetracycline resistant, plasmids can be increased with the alkaline phosphatase treatment as described.

Ultimately, plasmids pDP 250 A and pDP 250 B are identified by restriction analysis using Xho I to determine orientation.

As shown in FIGS. 11D and E, the virus mutants VP 11 and VP 12 are respectively derived from plasmids pDP 250 B and pDP 250 A by in vivo recombination of these plasmids with VTK⁻79 vaccinia virus. Crossover and recombination occur in the long and short "arms" of the vaccinia F-fragment present in the plasmids. That portion of the plasmids derived from pBR 322 is not incorporated into the virus.

FIG. 12A shows the structure of the pTHBV 1 plasmid, known in the art and shown earlier herein in FIG. 11B. As shown in the Figure, if the plasmid is treated with the restriction enzyme Hha I, two identical fragments will be obtained containing only that region of the HBV genome contained within the plasmid which codes for the surface antigen, free of any pre-surface antigen region. (In fact, there are many Hha I restriction sites within pTHBV 1, and numerous fragments will be produced upon digestion with this restriction enzyme. However, the fragment of interest discussed above is the largest of the numerous fragments obtained, and can be readily isolated because of this fact.) A linear DNA map of this Hha I fragment is also shown in FIG. 12A, with the further indication of a Bam HI site for purposes of orientation.

If the Hha I fragment of FIG. 12A is treated first with T4 DNA polymerase and then Hind III linkers are added with T4 DNA ligase, the fragment can be provided with Hind III sticky ends. As known in the art, T4 DNA polymerase has both a polymerase activity in the 5'- to 3'-direction, as well as exonuclease activity in the 3'- to 5'-direction. The two opposing activities will result in the "chewing off" of 3'-OH ends in the Hha I fragment shown in FIG. 12A until an equilibrium state is reached, with the resultant production of a blunt ended DNA fragment. The blunt ended fragment can be treated with Hind III linkers, known in the art, which are essentially decanucleotides containing therein the recognition sequence for Hind III.

As shown in the map in FIG. 12B, the resulting fragment will have Hind III sticky ends and can be introduced, as shown in FIG. 12B, into pBR 322 by treatment of the latter plasmid with Hind III and T4 DNA ligase. The resultant plasmid, identified in FIG. 12C, is designated as pDP 252.

Finally, as shown in FIG. 12D, this plasmid can be introduced into vaccinia mutant VP 8 by in vivo recombination to produce new vaccinia variant VP 13 (ATCC No. 2047). Expression of the HBV gene by VP 13 has not yet been detected.

FIGS. 13A–C show the production of two further virus mutants, VP 16 (ATCC No. VR 2050) and VP 14 (ATCC No. VR 2048), each containing the DNA sequence of herpes virus type I which codes for production of the herpes glycoproteins gA+gB.

More in particular, FIG. 13A is a map of the Eco RI fragment F of herpes virus type I, strain KOS [Little et al, Virology 112, 686–702 (1981)]. As is evident from the Figure, the DNA sequence contains numerous Bam HI sites (indicated as B) within the sequence, including one DNA region 5.1 md in length between adjacent Bam HI sites and representing the largest Bam HI fragment within the Eco RI fragment under discussion.

As further shown in FIG. 13A, this Eco RI fragment can be introduced into pBR 322 by treatment with Eco RI and $T_4$ DNA ligase to produce two new plasmids, respectively identified as pBL 520 A and 520 B, distinguished by the orientation of the Eco RI fragment therein (as indicated by the Hpa I sites, used for orientation.)

Finally, as shown in FIG. 13C, these plasmids can be introduced into vaccinia virus mutant VP 7 (containing the pBR 322 genome) by in vivo recombination analogous to that discussed for FIGS. 10 and 12 thus producing vaccinia mutants VP 16 and VP 14 respectively.

Thus, this is a further example of the use of the pBR 322 DNA sequence (rather than the DNA sequence of the vaccinia F-fragment) to effect in vivo recombination for the production of further vaccinia virus mutants. Also, vaccinia variants VP 16 and 14 produced by this method are of interest in containing more than 20,000 base pairs of foreign DNA incorporated into the genome of vaccinia virus. This represents a minimum upper limit of foreign DNA insertion into vaccinia.

FIGS. 14A–C show the production of two further virus mutants, VP 17 and VP 18, into which have been introduced a Bam HI segment of the herpes virus type I (strain KOS) Eco RI fragment F. The Eco RI fragment F is shown in FIG. 13A as including this 5.1 megadalton Bam HI fragment G.

FIG. 14A shows this Bam HI fragment, including the location therein of two Sst I sites which are asymmetric and are used for orientation.

This Bam HI segment of the herpes virus, which still codes for the production of herpes glycoproteins gA+gB [cf. De Luca et al., ibid.], is introduced into pDP 120 (cf. FIG. 7C) by partial digestion with Bam HI and $T_4$ DNA ligase, as further shown in FIG. 14A.

As shown in FIG. 14B, two new plasmids, pBL 522 A and pBL 522 B, are obtained, each having a molecular weight of 11.6 megadaltons and each containing the Bam HI fragment G of the herpes virus genome in one of two different orientations.

Finally, as shown in FIG. 14C, these plasmids can be introduced into VTK−79 by in vivo recombination to produce vaccinia mutants VP 17 (ATCC NO. 2051) and VP 18 (ATCC No. VR 2052). Expression of the herpes glycoprotein gene by mutants VP 17 and 18 has not yet been determined.

FIGS. 15A–F illustrate the construction of a further vaccinia variant, VP 22 (ATCC No. VR 2054) wherein foreign DNA is present in the vaccinia genome in a non-essential region different from the F-fragment utilized for the production of other vaccinia variants described herein.

More in particular, FIG. 15A shows the Ava I H-fragment of the vaccinia virus L-variant genome. As shown in FIG. 6A, the Ava I fragment is entirely within the region deleted from the S-variant and, hence, is known to be non-essential for the viability of the virus.

As shown in FIG. 15A, this Ava I H-fragment is combined with a Hind III-cleaved pBR 322 plasmid to form a new plasmid, pDP 202, shown in FIG. 15B. The ligation is accomplished by "blunt-ending" both the Ava I H-fragment of vaccinia and the termini of the Hind III-cleaved pBR plasmid, using $T_4$ DNA polymerase. When the blunt-ended DNA sequences are combined in the presence of $T_4$ DNA ligase, pDP 202 is formed.

As further suggested in FIG. 15B, the new plasmid, pDP 202, is combined with a herpes Bgl/Bam TK fragment. The latter fragment is obtained from the herpes Bam TK DNA fragment (cf. FIG. 3B) by treatment with Bgl II. The treatment with Bgl II removes the endogenous herpes promoter region contained within the Bam TK fragment.

Because, as earlier noted, Bgl II and Bam HI produce the same "sticky ends" on DNA treated therewith, the resulting herpes Bgl/Bam TK fragment can be inserted into a Bam site within pDP 202.

As suggested by FIG. 15C, such an insertion is effected by partial digestion with Bam HI and treatment with $T_4$ DNA ligase.

Since the H-fragment of vaccinia present in pDP 202 contains three Bam HI sites, a total of six plasmids can be produced by insertions in this region, namely two variants for each of the three Bam HI sites, depending on the orientation in each site of the herpes Bgl/Bam TK DNA sequence. The orientation of the latter can be recognized by the presence therein of a non-symmetric Sst I site near the Bgl II end of the fragment.

As shown in FIG. 15C, two plasmids, pDP 202 TK/A and pDP 202 TK/D are obtained when the herpes Bgl/Bam TK fragment is inserted in the first of the three Bam HI sites present within the H-fragment of vaccinia present in pDP 202. Similarly, two other plasmids, pDP 202 TK/E and /C are obtained upon insertion of the Bgl/Bam DNA sequence in the second of the three available sites. Finally, two further plasmids, pDP 202 TK/B and /F are obtained upon insertion of the Bgl/Bam fragment in each of two possible orientations in the third Bam HI site. Of these plasmids, pDP 202 TK/E has proved of particular interest.

Figure 15A:
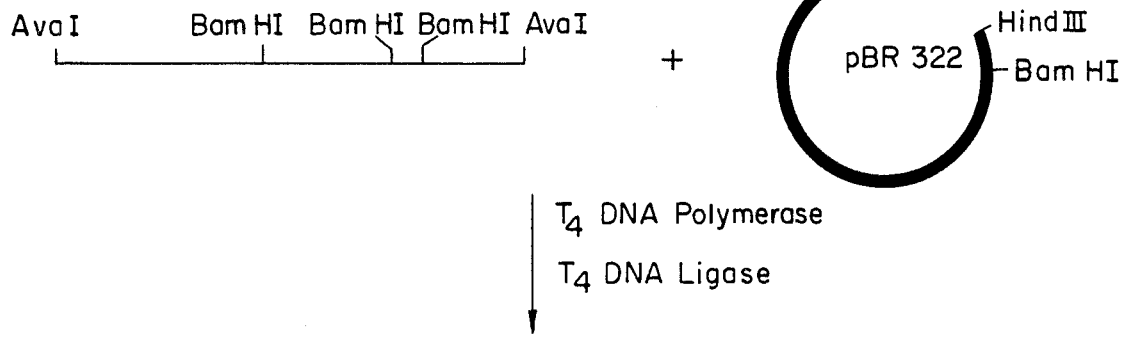
Figure 15B:
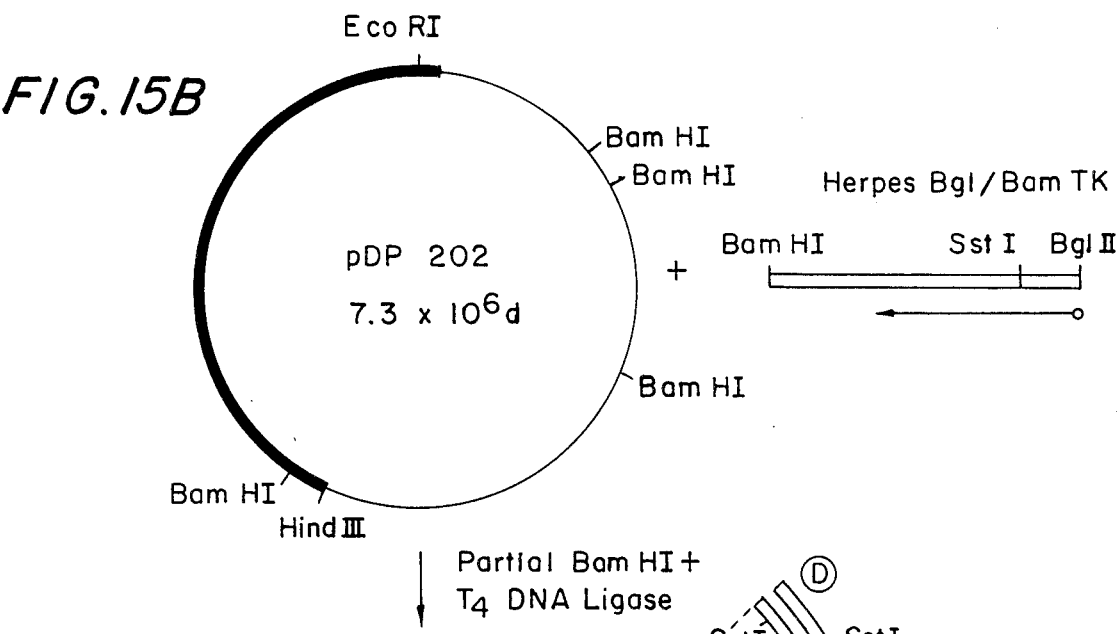
Figure 15C:
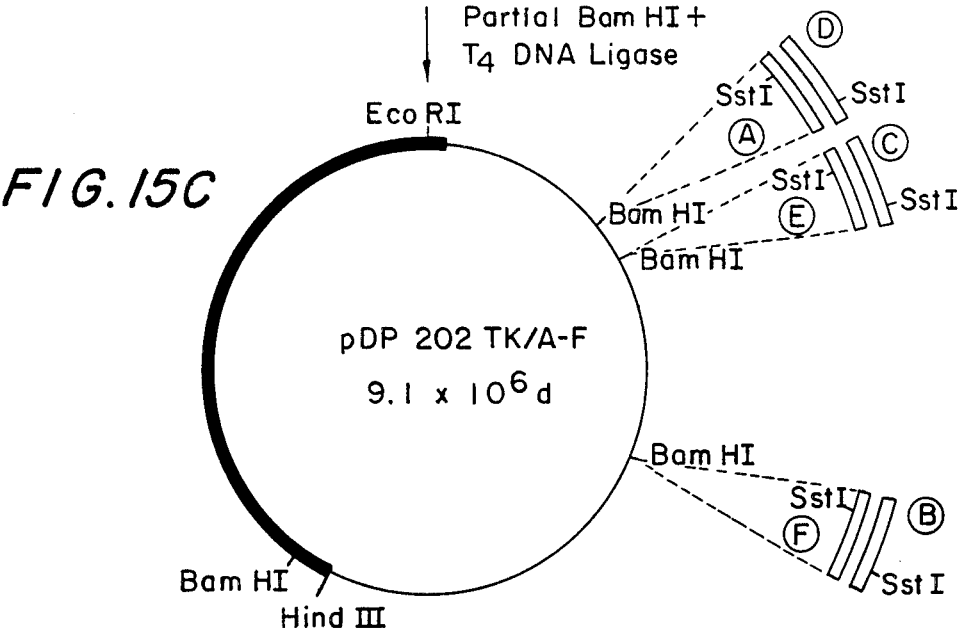
Figure 15D:
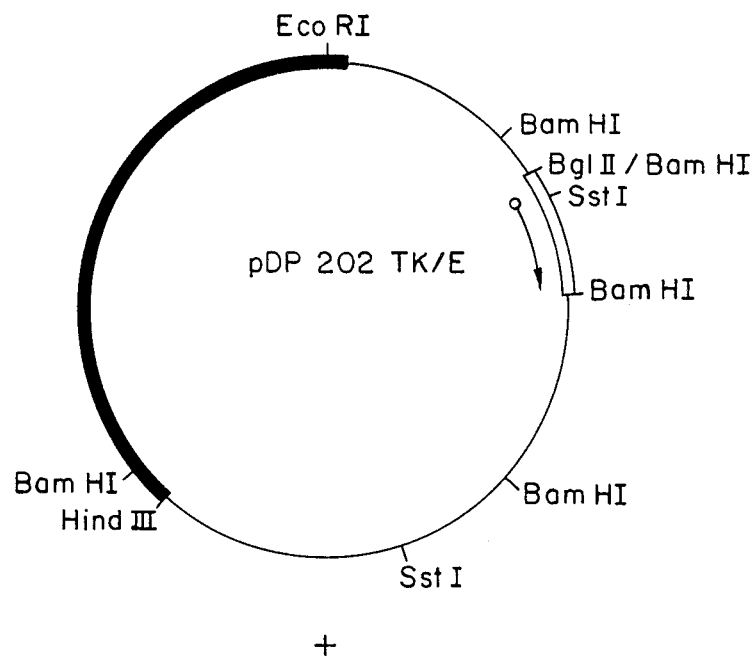

The plasmid is shown in greater detail in FIG. 15D, wherein the orientation of the Bgl/Bam fragment is indicated.

Figure 15E:
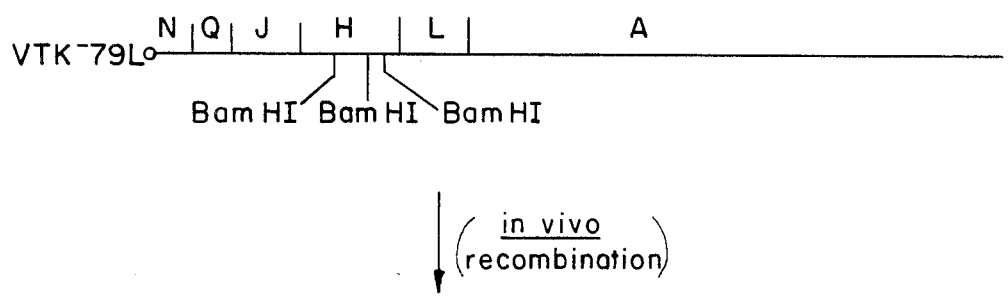
Figure 15F:
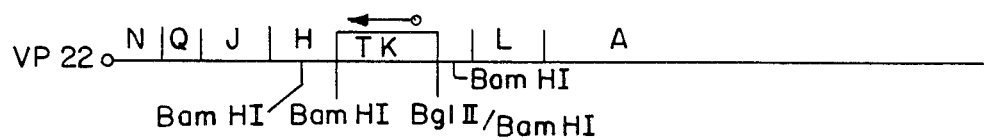

The plasmid can be incorporated by in vivo recombination into the genome of VTK−79 L. FIG. 15E is an Ava I map of the left-hand portion of this vaccinia genome. A map of the modified genome, which is the genome of VP 22, is shown in FIG. 15F.

This vaccinia variant is of particular interest since it shows a higher level of TK expression than do variants VP 2, VP 4, and VP 6, in which the Bam TK fragment is present within the F-fragment of vaccinia. Further, VP 22 demonstrates the introduction of foreign DNA into non-essential portions of the vaccinia genome other than the F-fragment which has been used, as a matter of convenience, for the constructions of other vaccinia variants reported herein.

Finally, since all the herpes virus regulatory sequences are deleted from the Bgl/Bam herpes virus DNA sequence by treatment with Bgl II, as described earlier herein, the VP 22 vaccinia variant demonstrates conclusively that transcription in this recombinant virus is initiated by regulatory signals within the vaccinia genome.

A better understanding of the present invention and of its many advantages will be had by referring to the following specific Examples, given by way of illustration. The percentages given are percent by weight unless otherwise indicated.

EXAMPLE I

Isolation of Vaccinia Hind III Fragments from Agarose Gels

Restriction endonuclease Hind III was purchased from Boehringer Mannheim Corp. Preparative digestions of DNA were performed in 0.6 ml of HInd III buffer containing 10 millimolar (mM) Tris-HCl (pH 7.6), 50 mM NaCl, 10 mM $MgCl_2$, 14 mM dithiothreitol (DTT), and 10 micrograms ($\mu g$)/ml of bovine serum albumin (BSA) in which are present 10–20 $\mu g$ of vaccinia DNA and 20–40 units of Hind III (1 unit is the amount of enzyme sufficient to cleave 1 $\mu g$ of lambda-DNA completely in 30 minutes.)

Vaccinia DNA was extracted and purified from virions as follows. Purified virions were lysed at a concentration having an optical density per ml of 50 measured at 260 nanometers ($A_{260}$) in 10 mM Tris-HCl (pH 7.8), 50 mM beta-mercaptoethanol, 100 mM NaCl, 10 mM $Na_3EDTA$, 1% Sarkosyl NL-97, and 26% sucrose. Proteinase K was added to 100 $\mu g$/ml and the lysate incubated at 37° C. overnight. DNA was extracted by the addition of an equal volume of phenol-chloroform (1:1). The organic phase was removed and the aqueous phase reextracted until the interface was clear. Two additional extractions with chloroform were performed and the aqueous phase was then dialyzed extensively against 10 mM Tris-HCl (pH 7.4) containing 0.1 mM $Na_3$ EDTA at 4° C. DNA was concentrated to approximately 100 $\mu g$/ml with Ficoll (a synthetic high copolymer of sucrose and epichlorohydrin).

Digestion of the DNA was for 4 hours at 37° C. The reactions were terminated by heating to 65° C. for 10 minutes followed by addition of an aqueous stop solution containing 2.5% of agarose, 40% of glycerol, 5% of sodium dodecyl sulfate (SDS), and 0.25% of bromophenol blue (BPB). Samples were layered at 65° C. onto agarose gel and allowed to harden prior to electrophoresis.

Electrophoresis was carried out in 0.8% agarose gels ($0.3 \times 14.5 \times 30$ cm) in electrophoresis buffer containing 36 mM Tris-HCl (pH 7.8), 30 mM $NaH_2PO_4$, and 1 mM EDTA. Electrophoresis was at 4° C. for 42 hours at 50 volts. The gels were stained with ethidium bromide (1 $\mu g$/ml in electrophoresis buffer). The restriction fragments were visualized with ultraviolet (UV) light and individual fragments were cut from the gel.

Fragments were separated from the agarose gel according to the procedure of Vogelstein et al., Proc. Natl. Acad. Sci. USA 76, 615–619 (1979) using glass powder as follows. The agarose gel containing a DNA fragment was dissolved in 2.0 ml of a saturated aqueous solution of NaI. 10 mg of glass powder were added per $\mu g$ of DNA calculated to be present. The solution was rotated at 25° C. overnight to bind the DNA to the glass powder. The DNA-glass powder was collected by centrifugation at 2000 rpm for 5 minutes. The DNA-glass was then washed with 5 ml of 70% NaI. The DNA-glass was again collected by centrifugation and washed in a mixture of 50% buffer [20 mM Tris-HCl (pH 7.2), 200 mM NaCl, 2 mM EDTA] and 50% ethanol. The DNA-glass was collected again by centrifugation and was gently suspended in 0.5 ml of 20 mM Tris-HCl (pH 7.2), 200 mM NaCl, and 2 mM EDTA. The DNA was then eluted from the glass powder at 37° C. by incubation for 30 minutes. The glass was then removed by centrifugation at 10000 rpm for 15 minutes. DNA was recovered from the supernatant by ethanol precipitation and dissolved in 10 mM Tris-HCl (pH 7.2) containing 1 mM EDTA.

The F-fragment isolated in this way was used in the following Examples.

EXAMPLE II

Insertion of the Vaccinia Hind III-F Fragment Into the Hind III Site of pBR 322 (Construction of pDP 3 [pBR 322-Vaccinia Hind III Vaccinia Hind III-F fragment was isolated from preparative agarose gels as described in Example I. This fragment was inserted into the Hind III site of pBR 322 [Bolivar et al., Gene, 2, 95–113 (1977)] as follows.

Approximately 200 nanograms (ng) of pBR 322 were cleaved with Hind III in 10 mM Tris-HCl (pH 7.6), 50 mM NaCl, 10 mM $MgCl_2$, and 14 mM DTT [Hind III buffer] using 1 unit of enzyme for 1 hour at 37° C. The reaction was stopped by heating to 65° C. for 10 minutes. 500 ng of isolated Hind III vaccinia F-fragment were added and the DNAs co-precipitated with 2 volumes of ethanol at −70° C. for 30 minutes. The DNA was then washed with 70% aqueous ethanol, dried, and resuspended in ligation buffer consisting of 50 mM Tris-HCl (pH 7.6), 10 mM $MgCl_2$, 10 mM DTT, and 1 mM adenosine triphosphate (ATP). Approximately 100 units of $T_4$ DNA ligase (New England Biolabs) were then added and the mixture was incubated at 10° C. overnight. The ligase-treated DNA was then used to transform E. coli HB101 [Boyer et al., J. Mol. Biol. 41, 459–472 (1969)].

EXAMPLE III

Transformation of E. coli and Selection for Recombinant Plasmids

Competent cells were prepared and transformed with plasmids according to the procedure described by Dagert et al., Gene 6, 23–28 (1979). E. coli HB101 cells were made competent by inoculating 50 ml of LB broth (1% of bacto-tryptone, 0.5% of bacto-yeast extract, and 0.5% of NaCl supplemented with 0.2% of glucose) with 0.3 ml of an overnight culture of the cells and allowing them to grow at 37° C. until the culture had an optical density (absorbence), at 650 nanometers ($A_{650}$), of 0.2, as measured with a spectrophotometer. The cells were then chilled on ice for 10 minutes, pelleted by centrifugation, resuspended in 20 ml of cold 0.1 molar (M) $CaCl_2$, and incubated on ice for 20 minutes. The cells were then pelleted and resuspended in 0.5 ml of cold 0.1M $CaCl_2$ and allowed to remain at 4° C. for 24 hours. The cells were transformed by adding ligated DNA (0.2–0.5 mg in 0.01–0.02 ml of ligation buffer) to competent cells (0.1 ml). The cells were then incubated on ice for 10 minutes and at 37° C. for 5 minutes. 2.0 ml of LB broth were then added to the cells and incubated at 37° C. for 1 hour with shaking. Aliquots of 10 microliters (μl) or 100 ul were then spread on LB agar plates containing ampicillin (Amp) at a concentration of 100 μg/ml.

The transformed bacteria were then screened for recombinant plasmids by transferring ampicillin resistant ($Amp^R$) colonies to LB agar containing tetracycline (Tet) at 15 μg/ml. Those colonies which were both $Amp^R$ and tetracycline sensitive ($Tet^S$) (approximately 1%) were screened for intact vaccinia Hind III-F fragment inserted into pBR 322 according to the procedure of Holmes et al., Anal. Bioch. 114, 193–197 (1981). 2.0 ml cultures of transformed E. coli were grown overnight at 37° C. The bacteria were pelleted by centrifugation and resuspended in 105 μl of a solution of 8% sucrose, 5% Triton X-100, 50 mM EDTA, and 50 mM Tris-HCl (pH 8.0), followed by the addition of 7.5 μl of a freshly prepared solution of lysozyme (Worthington Biochemicals) [10 mg/ml in 50 mM Tris-HCl(pH 8.0)]. The lysates were placed in a boiling water bath for 1 minute and then centrifuged at 10000 rpm for 15 minutes. The supernatant was removed and plasmid DNA precipitated with an equal volume of isopropanol. The plasmids were then resuspended in 40 μl of Hind III buffer and digested with 1 unit of Hind III for 2 hours. The resulting digests were then analyzed on a 1.0% analytical agarose gel for the appropriate Hind III-F fragment. One such recombinant plasmid containing an intact Hind III-F fragment, denominated pDP 3, was used for further modification. (See FIG. 3B).

EXAMPLE IV

Preparative Isolation of pDP 3

Large scale isolation and purification of plasmid DNA was performed by a modification of the procedure of Clewel et al., Proc. Natl. Acad. Sci. USA 62, 1159–1166 (1969). 500 ml of LB broth were inoculated with 1.0 ml of an overnight culture of E. coli HB 101 containing pDP 3. At an optical density ($A_{600}$) of approximately 0.6, chloramphenicol was added (100 μg/ml) to amplify the production of plasmids [Clewel, J. Bacteriol. 110, 667–676 (1972)]. The bacteria were incubated at 37° C. for an additional 12–16 hours at which time they were collected by centrifugation at 5000 rpm for 5 minutes, washed once in 100 ml of TEN buffer [1 mM Tris-HCl (pH 8.0), 150 mM NaCl, 10 mM EDTA], collected by centrifugation and resuspended in 14 ml of a 25% solution of sucrose in 0.05M Tris-HCl (pH 8.0). 4.0 ml of lysozyme solution [5 mg/ml in 0.25M Tris-HCl (pH 8.0)] were added and the mixture was incubated at room temperature for 30 minutes followed by the addition of 4.0 ml of 0.25M EDTA (pH 8.0). The mixture was then put on ice for 10 minutes. 2.0 ml of pancreatic RNase A (Sigma Chemical Co.,) [1 mg/ml in 0.25M Tris-HCl (pH 8.0)] were added to this mixture, which is then incubated at room temperature for 1 minute. The cells were then lysed by adding 26 ml of a lytic Triton solution [1% Triton X-100, 0.05M EDTA, 0.05M Tris-HCl (pH 8.0)]. The mixture was incubated at room temperature for 30–60 minutes. The lysate was cleared by centrifugation at 17000 rpm for 30 minutes at 4° C. The supernatant was then removed and plasmid DNA separated from chromosomal DNA on dye-bouyant CsCl gradients.

For this purpose, CsCl-ethidium bromide gradients were prepared by dissolving 22 g of CsCl in 23.7 ml of cleared lysate. 1.125 ml of aqueous ethidium bromide (10 mg/ml) were added to the solution. The mixture was then centrifuged in polyallomer tubes in a Beckman 60 Ti rotor at 44000 rpm for 48–72 hours. The resulting bands of DNA in the gradients were visualized with ultraviolet light and the lower band (covalently closed plasmid DNA) was removed by puncturing the tube with an 18 gauge needle attached to a syringe. Ethidium bromide was removed from the plasmid by repeated extraction with 2 volumes of chloroform-isoamyl alcohol (24:1). Plasmids were then dialyzed extensively against 10 mM Tris-HCl (pH 7.4) containing 0.1 mM EDTA to remove CsCl. The plasmid DNA was then concentrated by ethanol precipitation.

EXAMPLE V

Construction of pBR 322/Vaccinia/Herpes Virus TK Recombinant Plasmids

FIGS. 3B and 3C summarize the steps involved in the construction of the recombinant plasmids used for inserting the Bam HSV TK fragment into S- or L-variant vaccinia. Approximately 15 μg of covalently closed pDP 3 were cleaved by partial digestion with Bam HI (Bethesda Research Laboratories) by incubation in Bam HI buffer, consisting of 20 mM Tris-HCl (pH 8.0), 7 mM $MgCl_2$, 100 mM NaCl, and 2 mM beta-mercaptoethanol, using 7 units of Bam HI for 10 minutes at 37° C. Since pBR 322 and vaccinia Hind III F each contain a Bam HI site, partial cleavage results in a mixture of linear plasmids cut either at the pBR 322 or vaccinia Bam HI site. These mixed linear plasmids were then separated from the fragments of pDP 3 cut at both the pBR 322 and vaccinia Bam HI sites by electrophoresis on agarose gels and the singly cut linear plasmids were isolated using glass powder as described in Example I.

A recombinant pBR 322 containing the 2.3 megadalton (md) HSV Bam HI fragment which codes for HSV TK, as described by Colbere-Garapin et al., Proc. Natl. Acad. Sci. USA 76, 3755–3759 (1979), was digested to completion with Bam HI and the 2.3 md Bam TK fragment was isolated from an agarose gel as described above.

pDP 3 Bam TK recombinant plasmids were constructed by ligating approximately 1 μg of Bam HI linearized pDP 3 to approximately 0.2 μg of isolated Bam TK fragment in 20μl of ligation buffer containing 100 units of T4 DNA ligase at 10° C. overnight. This ligation mixture was then used to transform competent E. coli HB 101 cells as described in Example III.

EXAMPLE VI

Screening of Transformed Cells for Identification of Those Containing Recombinant Plasmids Having HSV TK Inserts Transformed cells containing recombinant plasmids were screened for HSV TK insertions by colony hybridization essentially as described by Hanahan et al., Gene 10, 63-67 (1980).

A first set of nitrocllulose filters (Schleicher and Schull BA85) were placed on Petri dishes filled with LB agar containing 100 μg/ml of ampicillin. Transformed cells were spread on the filters and the dishes were incubated at 30° C. overnight or until the colonies were just visible. A replica nitrocellulose filter of each of the first set of filters was made by placing a sterile nitrocellulose filter on top of each of the above-mentioned original filters and pressing the two filters together firmly. Each pair of filters was then notched (keyed) with a sterile scalpel blade, separated, and each filter was transferred to a fresh LB agar plate containing ampicillin at 100 μg/ml for 4-6 hours. The first set of filters (original filters) were then placed on LB agar plates containing 200 μg/ml of chloramphenicol to amplify plasmid production. The replica filters were stored at 4° C.

After 24 hours on chloramphenicol, the original nitrocellulose filters were prepared for hybridization as follows. Each nitrocellulose filter was placed on a sheet of Whatman filter paper saturated with 0.5 N NaOH for 5 minutes, blotted on dry filter paper for 3 minutes, and placed back on the NaOH saturated filter paper for 5 minutes to lyse the bacteria thereon and to denature their DNA. This sequence was then repeated using Whatman filter paper sheets saturated with 1.0M Tris-HCl (pH 8.0) and repeated a third time with filter paper sheets saturated with 1.0M Tris-HCl (pH 8.0) containing 1.5M NaCl for purposes of neutralization. The nitrocellulose filters treated in this manner were then air dried and baked in vacuo at 80° C. for 2 hours.

Prior to hybridization these nitrocellulose filters were next treated for 6-18 hours by incubating at 60° C. in a prehybridization buffer which is an aqueous mixture of 6×SSC [1×SSC=0.15M NaCl and 0.015M Na citrate (pH 7.2)], 1×Denharts [1×Denharts=a solution containing 0.2% each of Ficoll, BSA, and polyvinylpyrrolidone], and 100-200 μg of denaturated sheared salmon sperm DNA (S.S. DNA)/ml, 1 mM EDTA, and 0.1% SDS. This treatment will decrease the amount of binding between the filter and non-hybridized probe DNA next to be applied to the filters.

To screen for recombinant plasmids containing HSV TK inserts, the transformed colonies fixed to the original, treated, nitrocellulose filters were hybridized with $^{32}P$ labelled Bam HSV TK fragment by immersion of the filters in hybridization buffer containing 2×SSC (pH 7.2), 1×Denhart's solution, 50 μg of S.S. DNA/ml, 1 mM EDTA, 0.1% of SDS, 10% of dextran sulfate, and $^{32}P$ Bam TK as the hybridization probe. The level of radioactivity of the solution was approximately 100,000 counts per minute (cpm) per milliliter.

Hybridization was effected at 60° C. over 18-24 hours [Wahl et al. Proc. Natl. Acad. Sci. USA 76, 3683-3687 (1979)].

[To prepare the hybridization probe, the 2.3 md Bam TK fragment was labelled by nick translation according to the method of Rigby et al., J. Mol. Biol. 113, 237-251 (1977). More specifically, 0.1 ml of a reaction mixture was prepared containing 50 mM Tris-HCl (pH 7.6), 5 mM MgCl$_2$, 20 μM deoxycytidine triphosphate (dCTP), 20 μM deoxyadenosine triphosphate (dATP), 20 μM deoxyguanosine triphosphate (dGTP), 2 μM (alpha-$^{32}$P)deoxythymidine triphosphate (dTTP) (410 Curies/m mol) (Amersham Corporation), 1 ng of DNase I, 100 units of DNA polymerase I (Boehringer Mannheim), and 1 μg of Bam TK fragment. The reaction mixture was incubated at 14° C. for 2 hours. The reaction was terminated by adding 50 μl of 0.5M EDTA and heating to 65° C. for 10 minutes. Unincorporated triphosphates were removed by gel filtration of the reaction mixture on Sephadex G50.

After hybridization, excess probe was removed from the nitrocellulose filters by washing 5 times in 2×SSC (pH 7.2) containing 0.1% of SDS at room temperature, followed by 3 washes in 0.2×SSC (pH 7.2) containing 0.1% of SDS at 60° C., with each wash lasting 30 minutes. The washed filters were then air dried and used to expose X-ray film (Kodak X-omat R) at −70° C. for 6-18 hours using a Cronex Lightening Plus intensifying screen (du Pont) for enhancement.

The exposed and developed X-ray film was then used to determine which colonies contained pBR 322 vaccinia Bam HSV TK recombinant plasmids. Those colonies which exposed the X-ray film were located on the corresponding replica nitrocellulose filter. Such positive colonies were then picked from the replica filters for further analysis. Of the approximately 1000 colonies screened in this manner, 65 colonies were tentatively identified as having a Bam TK insert within pDP 3.

EXAMPLE VII

Restriction Analysis of Recombinant Plasmids Containing Bam HSV TK

Each of the 65 colonies which were tentatively identified as containing recombinant plasmids with Bam HSV TK inserts were used to inoculate 2.0 ml cultures of LB broth containing ampicillin at 100 μg/ml. The cultures were then incubated at 37° C. overnight. Plasmids were extracted from each culture as described in Example III. The plasmids were dissolved in a 50 μl of water after isopropanol precipitation.

To determine if the plasmids contained an intact 2.3 md Bam HSV TK fragment and at which Bam HI site within pDP 3 the Bam HSV TK was inserted, 25 μl of each plasmid preparation were mixed with 25 μl of 2×Hind III buffer and digested at 37° C. for 2 hours with 1 unit of Hind III. The resulting fragments were then analyzed by electrophoresis on a 1.0% agarose gel as described previously.

Of the 65 plasmid preparations analyzed, 6 were found to contain Bam HSV TK fragments inserted into the Bam HI site present in the vaccinia Hind III F portion of the plasmid, i.e. they yielded Hind III restriction fragments of molecular weights corresponding to linear pBR 322 (2.8 md) and fragments of a molecular weight greater than that of the vaccinia Hind III F fragment (8.6 md).

These 6 plasmids were further analyzed with Sst I (an isoschizomer of Sac 1) to determine the number and orientation of the Bam HSV TK fragments inserted within vaccinia Hind III F Fragment, since Sst I (Sac I) cleaves both the Bam HSV TK fragment and the vaccinia Hind III F fragment asymetrically. The analyses were performed by mixing 25 µl of the plasmid with 25 µl of 2×Sst buffer [50 mM Tris-HCl (pH 8.0), 10 mM of $MgCl_2$, 100 mM of NaCl, and 10 mM of DTT] and digesting with 1 unit of Sst I (Bethesda Research Laboratories') at 37° C. for 2 hours. The resulting fragments were analyzed by electrophoresis in 1% agarose gels. Of the 6 plasmids analyzed, 5 yielded two Sst I fragments with molecular weights of 10.1 md and 3.5 md, indicating a single Bam HSV TK insert. One of these plasmids was selected for further study and designated pDP 132. The other plasmid yielded three Sst I fragments with molecular weights of 10.8 md, 2.8 md, and 2.3 md, indicating tandom Bam HSV TK inserts oriented head to tail and in the opposite orientation as compared to pDP 132. This plasmid was designated pDP 137. The plasmids pDP 132 and pDP 137 are diagramed in FIG. 3C.

EXAMPLE VIII

Isolation of a TK$^-$ S-variant Vaccinia Virus

To isolate a TK$^-$ S-variant vaccinia virus mutant, a virus population was subjected to strong selective pressure for such a mutant by growing the virus in cells in the presence of BUdR, which is lethal to organisms carrying the TK gene. More in particular, confluent monolayers of TK$^-$ human (line 143) cells growing in Eagle's Special medium in 150 mm Petri dishes were infected with approximately $3 \times 10^3$ plaque forming units (pfu) of S-variant vaccinia virus per dish (20 dishes used) in the presence of 20 µg BUdR/ml. (Eagle's Special medium is a commercially available nutrient medium for the growth of most cell lines. Alternative media such as Eagle's Minimum Essential Medium, Basal Eagle's Medium, Ham's-F10, Medium 199, RPMI-1640, etc., could also be used.) Growth is at 37° C. in an atmosphere enriched in $CO_2$. This is conveniently done using a $CO_2$-incubator providing air enriched with $CO_2$ to have a $CO_2$ content of about 5 percent.

Ninety-three of the plaques which developed were isolated and replaqued on TK$^-$ (line 143) cells under the conditions mentioned previously and again in the presence of 20 µg of BUdR/ml. A number (5) of large, well isolated plaques were picked for further analysis.

The five plaque isolates were tested for growth on cell monolayers under the same conditions used earlier and in the presence or absence of 20 µg BUdR/ml. The relative growth of each plaque in the presence and absence of BUdR was noted and compared with the relative growth in similar monolayer cell cultures of the parent S-variant virus. The following results were obtained:

| Plaque Isolate | −BUdR (pfu/ml) | +BUdR (pfu/ml) |
|---|---|---|
| #70 | $5.1 \times 10^5$ | $4.1 \times 10^5$ |
| #73 | $1.0 \times 10^6$ | $1.0 \times 10^6$ |
| #76 | $4.7 \times 10^5$ | $4.7 \times 10^5$ |
| #79 | $5.4 \times 10^5$ | $4.4 \times 10^5$ |
| #89 | $5.9 \times 10^5$ | $7.0 \times 10^5$ |

| Plaque Isolate | −BUdR (pfu/ml) | +BUdR (pfu/ml) |
|---|---|---|
| S-variant | $1.7 \times 10^{10}$ | $9.7 \times 10^6$ |

The growth of plaque isolate #79 was further monitored in the presence of 0, 20 and 40 µg BUdR/ml and compared with the growth of its parent S-variant virus. The following results were obtained:

| Virus | Yield (pfu/ml) | | |
|---|---|---|---|
| | 0 µg/ml | 20 µg/ml | 40 µg/ml |
| #79 | $2.5 \times 10^5$ | $4.1 \times 10^5$ | $3.2 \times 10^5$ |
| S-Variant | $1.2 \times 10^9$ | $1.3 \times 10^6$ | $2.0 \times 10^5$ |

In addition, the above 5 plaque isolates and the S-variant parent were monitored for growth on TK$^-$ human (line 143) cells in the presence of MTAGG. MTAGG is an Eagle's Special medium modified by the presence of:

| | |
|---|---|
| $8 \times 10^{-7}$ M | methotrexate |
| $1.6 \times 10^{-5}$ M | thymidine |
| $5 \times 10^{-5}$ M | adenosine |
| $5 \times 10^{-5}$ M | guanosine |
| $1 \times 10^{-4}$ M | glycine |

(cf. Davis et al., op. cit.) and selects for thymidine kinase and against organisms free of the thymidine kinase gene. The results of such an experiment were as follows:

| Virus | Plaque Forming Units/ml | |
|---|---|---|
| | −MTAGG | +MTAGG |
| #70 | $4.0 \times 10^5$ | 0 |
| #73 | $5.8 \times 10^5$ | 0 |
| #76 | $2.8 \times 10^5$ | $3.3 \times 10^3$ |
| #79 | $3.6 \times 10^5$ | 0 |
| #80 | $4.3 \times 10^5$ | $4.0 \times 10^3$ |
| S-Variant | $4.8 \times 10^9$ | $2.6 \times 10^9$ |

Of the three plaque isolates showing complete inhibition of growth in the presence of MTAGG, isolate #79 was arbitrarily selected and extracts prepared from cells infected with #79 virus were compared with extracts prepared from uninfected cells and from cells infected with the S-variant parent virus with respect to the ability of the extracts to phosphorylate tritiated ($^3$H) thymidine. The results are tabulated below:

| Extract Source | $^3$H Thymidine Phosphorylated (cpm/15 µg Protein) |
|---|---|
| Uninfected TK$^-$ human (line 143) | |
| #79 infected cells | 90 |
| S-variant infected cells | 66,792 |

In view of (1) resistance to BUdR, (2) inhibition of growth by a medi containing MTAGG, and (3) failure to detect significant phosphorylation of thymidine in infected cell extracts, plaque isolate #79 is considered to lack thymidine kinase activity. The isolate is designated VTK$^-$79.

EXAMPLE IX

Marker Rescue of L-variant Vaccinia DNA by the S-Variant

Four preparations of L-variant DNA were prepared for marker rescue studies. The first consisted of purified, intact, L-variant vaccinia DNA. The second consisted of L-variant vaccinia DNA digested with Bst E II, a restriction endonuclease which generates a donor DNA fragment, fragment C, comprising that DNA which is absent from the S-variant and uniquely present in the L-variant and which also has, at both ends of the DNA chain, a region of DNA homologous with corresponding sequences in the S-variant. The third and fourth preparations respectively consisted of L-variant DNA digested with Ava I and Hind III, restriction endonucleases that cleave the vaccinia genome within the unique L-variant DNA sequence. The marker rescue studies performed with these four preparations demonstrate that those L-variant DNA fragments containing the deleted region absent from the S-variant can be reintroduced into the S-variant by an in vivo recombination technique providing that the fragment contains, in addition to the deleted region, terminal regions which are homologous with corresponding sequences in the S-variant.

A better understanding of the fragments employed in these studies will be had by referring to FIGS. 6A–C, each of which is a restriction map of a portion of the left terminus of the vaccinia genome. More in particular, each map refers to the left-terminal region of the genome comprising approximately 60 kilobasepairs, as indicated in the Figure. The portion of the vaccinia genome which is deleted from the S-variant is represented in each map as the region between the dotted lines shown in the Figures, a region approximately 10 kilobasepairs in length.

Turning now more specifically to FIG. 6A, it is evident that fragment H obtained by digestion with Ava I is completely within the deleted region but will have no terminal DNA fragments homologous with the DNA of the S-variant because the Ava I cleavage sites fall entirely within the deleted region of the S-variant.

The restriction map of FIG. 6B pertaining to Hind III shows that this restriction enzyme similarly fails to produce a L-variant DNA fragment overlapping the deleted region of the S-variant. In this instance, sequences homologous with the S-variant are found at the left terminus of the C-fragment of Hind III. However, the restriction site at the right-hand terminus of fragment C falls within the deleted region and there is no terminal sequence homologous with the DNA sequence of the S-variant.

In contrast, the restriction map shown in FIG. 6C pertaining to Bst E II shows that digestion with this enzyme produces a fragment, fragment C, which includes the deleted region absent from the S-variant and also has terminal portions at both the left and right ends which are homologous with corresponding portions of the S-variant.

The results of the experiments, discussed more in detail below, indicate that the DNA which is present in he L-variant but is deleted from the S-variant is rescued by the S-variant with high efficiency from the intact L-variant genome, is rescued with lower efficiency from the C fragment of Bst E II, and cannot be rescued from either of the L-variant DNA fragments prepared with the Ava I and Hind III restriction endonucleases.

The high efficiency with which the deleted sequence is rescued from the intact L-variant is attributable to the fact that a single crossover between the intact L-variant and the S-variant is sufficient to produce an L-variant genome type. On the other hand, to rescue the deleted portion from the C fragment of Bst E II, a crossover between the fragment and the S-variant is necessary in both the left- and right-hand terminal portions of the C-fragment in order to incorporate the deleted region into the S-variant. Finally, since neither digestion with Ava I nor with Hind III produces DNA fragments which can be incorporated into the S-variant by any crossover, no rescue of the deleted portion is effected.

The marker rescue was performed on CV-1 monolayers using the calcium phosphate technique of Graham et al., Virology, 52, 456–467 (1973), as modified by Stow et al. and Wigler et al., both mentioned earlier herein. Confluent CV-1 monolayers were infected with S-variant vaccinia virus to give approximately 50 to 200 plaques in each of a number (5-20) of Petri-dishes of 6 cm diameter. To infect the cells, the growth medium (e.g. Eagle's Special containing 10% calf serum) is aspirated and a dilution of the virus containing 50-200 pfu/10.2 ml in a cell-compatible medium such as Eagle's Special containing 2% calf serum is applied to the cell monolayer. After incubation for a period of one hour at 37° C. in a $CO_2$-incubator to permit the absorption of the virus to the cells, various of the four L-variant DNA preparations earlier mentioned were each separately added to the monolayers as a calcium phosphate precipitate containing one microgram per dish of the L-variant DNA preparation. After 40 minutes, Eagle's Special medium with 10% calf serum was added and, four hours after the initial addition of the DNA, the cell monolayer was exposed to 1 ml of buffered 25 percent dimethyl sulfoxide for four minutes. This buffer contains 8 g of NaCl, 0.37 g of KCl, 0.125 g of $Na_2HPO_4.2-H_2O$, 1 g of dextrose, and 5 g of N-(2-hydroxyethyl)-piperazine,N'-(2- ethanesulfonic acid) (Hepes) per liter, having a final pH of 7.05. The dimethylsulfoxide was removed and the monolayers were washed and overlayed with nutrient agar. After three days, at 37° C. in a $CO_2$-incubator, the cells were stained with a nutrient agar overlayer containing Neutral red dye, which stains the uninfected cells (nutrient agar=Eagle's Special medium containing 10% calf serum and 1% agar). The next day, the agar overlay was removed and the monolayers were transferred to nitrocellulose filters and prepared for in situ hybridization as described by Villarreal et al., loc. cit. Since digestion of the L-variant genome with Ava I generates a 6.8 kilobasepair fragment, fragment H, that resides entirely with the unique DNA sequences deleted in the S-variant genome (cf. FIG. 6A), $^{32}P$-labelled nick-translated Ava I H fragment provides a highly specific probe for detecting the rescue of the unique L-variant DNA sequence by the S-variant.

For hybridization, the nitrocellulose filters were interleaved with Whatman No. 1 filter paper circles in 6 cm Petri dishes and were prehybridized for 6 hours at 60° C. in prehybridization buffer (SSC, Denhardt solution, EDTA, and S.S.DNA) as described earlier herein in Example VI. The radioactive probe consisting of 32P-labelled nick-translated L-variant Ava I, H fragment, having a specific activity of approximately $1 \times 10^8$ cpm/μg was used for hybridization in $2 \times SSC$, 1×Denhardt, 1 mM EDTA, 0.1 percent SDS, 10 percent of dextran sulfate, and 50 μg/ml of sonicated S.S.DNA at approximately 1×10⁵ cpm/ml overnight at 60° C. The radioactive probe was prepared according to the method of Rigby et al., J. Mol. Biol. 113, 237–251 (1977). The filters were washed repeatedly at room temperature and at 60° C. using the washing procedure of Example VI, were air dried, and radioautographed.

The results of the experiments are summarized in Table I below:

TABLE I

| Donor L-variant DNA Preparation | Percent of Plaques Containing L-variant Genotype |
| --- | --- |
| Intact L-variant | 5 |
| Bst E II total digest | 0.1 |
| Ava I total digest | 0 |
| Hind III total digest | 0 |

A minimum of 5000 plaques were analyzed for each donor DNA preparation.

EXAMPLE X

In vivo Recombination Using pDP 132 and pDP 137 to Generate Vaccinia Virus Mutants VP-1 through VP-6 and Identification Thereof Using Replica Filters A first calcium orthophosphate ecipitate of donor DNA was prepared by combining 5 ug of pDP 132 Hind III digested DNA in 50 μl of water, 4 μg of S-variant carrier DNA (prepared as in Example I) in 40 μl of water, and 10 μl of 2.5M $CaCl_2$, combining the resultant mixture with an equal volume of 2×Hepes phosphate buffer comprising 280 mM NaCl, 50 mM Hepes, and 1.5 mM sodium phosphate (pH=7.1), and permitting the precipitate to form over a period of 30 minutes at room temperature. A second precipitate was prepared in the same fashion, in the same amounts, but using pDP 137 Hind III digested DNA.

[As described more in detail by Stow et al. loc. cit. and Wigler et al., loc. cit., the modifications of the Graham et al. precipitation technique referred to earlier employ carrier DNA as a high molecular weight substance increasing the efficiency of calcium orthophosphate precipitate formation. The carrier DNA employed is DNA from the virus which is used for infection of the monolayered cells in the in vivo recombination technique.]

For in vivo recombination, confluent monolayers of CV-1 growing in Eagle's Special medium containing 10% calf serum were infected with S-variant vaccinia virus at a multiplicity of infection of 1 pfu/cell. The infection procedure is like that described in Example IX. The virus was permitted to absorb for 60 minutes at 37° C. in a $CO_2$-incubator, after which the innoculum was aspirated and the cell monolayer was washed. The precipitated DNA preparations were applied to separate cell monolayers and, after 40 minutes at 37° C. in a $CO_2$-incubator, liquid overlay medium was added (Eagle's Special containing 10% calf serum). In each case, the virus was harvested after 24 hours at 37° C. in a $CO_2$-incubator by 3 freeze/thaw cycles and titered on CV-1 monolayers. Approximately 15000 plaques were analyzed on CV-1 monolayers for recombinant virus using replica filters prepared as follows.

Plaques formed on confluent CV-1 monolayers under a nutrient agar overlay were transferred to a nitrocellulose filter by removing the agar overlay cleanly with a scalpel and placing the nitrocellulose filter onto the monolayer. Good contact between the filter and monolayer was effected by placing a Whatman No. 3 filter paper, wetted in 50 mM Tris buffer (pH=7.4) and 0.015 mM NaCl over the nitrocellulose filter and tamping with a rubber stopper until the monolayer transferred to the nitrocellulose shows a uniform color surrounding discrete uncolored plaques. (The monolayer has been previously stained with Neutral red, which is taken up by viable cells, i.e. cells unlysed by virus infection).

The nitrocellulose filter having the transferred monolayer thereon is now removed from the Petri dish and placed with the monolayer side up. A second nitrocellulose filter, wetted in the above-mentioned Tris-NaCl solution, is now placed directly over the first nitrocellulose filter and the two filters are brought firmly into contact by tamping with a rubber stopper after protecting the filters with a dry Whatman No. 3 circle. After removing the filter paper, the nitrocellulose filters are notched for orientation and separated. The second (replica) nitrocellulose filter now contains a mirror image of the cell monolayer transferred to the first nitrocellulose filter. The second filter is conveniently placed in a clean Petri dish and frozen. The first nitrocellulose filter is subjected to hybridization employing $^{32}P$-labelled Bam HSV TK fragment as a probe. The preparation of the probe and the hybridization technique are described earlier herein in Example VI.

Approximately 0.5 percent of the plaques analyzed by hybridization were positive, i.e. were recombinant virus containing Bam HSV TK.

Plaques of recombinant virus corresponding to those identified on the first nitrocellulose filter by hybridization were then isolated from the nitrocellulose replica filter by the following technique for further purification.

Using a sharp cork borer having a diameter slightly larger than the plaque to be picked, a desired plaque is punched out from the first or original nitrocellulose filter which has been used for identification of recombinants by hybridization. The resulting perforated filter is next used as stencil to identify and isolate the corresponding plaque on the replica filter. Namely, the replica filter is placed with the monolayer side up on a sterile surface and covered with a sheet of Saran wrap. The perforated first or original nitrocellulose filter is then placed monolayer side down over the second filter and the orientation notches present in the filters are aligned to bring the mirror images of the plaques into register. Again, using a cork borer, a plug is removed from the replica filter and, after removal of the Saran wrap protective layer, is placed in one ml of Eagle's Special medium containing 2% calf serum. The nitrocellulose plug is sonicated in this medium for 30 seconds on ice to release the virus. 0.2 ml of this virus preparation, and 0.2 ml of a 1:10 dilution of the preparation, are plated on CV-1 monolayers present in 6 cm Petri dishes.

As a plaque purification step, the entire sequence of preparing a first nitrocellulose filter, a replica filter, hybridization, and plaque isolation from the replica filter was repeated.

One sample of a purified plaque prepared in this manner starting from a calcium orthophosphate precipitate of pDP 132 Hind III digested DNA was denominated vaccinia virus VP-1. Similarly, a plaque containing a recombinant prepared from pDP-137 Hind III digested DNA was denominated VP-2. Both samples were grown up on suitable cell cultures for further study, including identification by restriction analysis and other techniques.

In like fashion, two further vaccinia mutants respectively denominated VP-3 and VP-4 were prepared by in vivo recombination employing VTK$^-$79 (an S-variant TK$^-$vaccinia virus as described in Example VIII) as the rescuing virus and, respectively, pDP 132 and pDP 137 as the plasmid donor DNA. The precipitates were formed as described earlier herein except that 5 μg of plasmid donor DNA present in 50 μl of water, 4 μg of VTK$^-$79 carrier DNA in 150 μl of water, and 50 μl of 2.5M $CaCl_2$ were combined and added dropwise to an equal volume of 250 μl of the Hepes phosphate buffer earlier described.

Further, the cells employed for infection by the VTK$^-$79 virus carrier were BHK-21 (Clone 13) cells instead of CV-1.

Two further vaccinia virus mutants denominated VP-5 and VP-6 were prepared using calcium orthophosphate precipitates of pDP 132 and pDP 137, respectively, each as prepared for mutants VP-3 and VP-4. However, in the case of mutants VP-5 and VP-6, the carrier DNA is vaccinia virus VTK$^-$11, rather than VTK$^-$79.

Again, BHK-21 (C-13) cell monolayers were infected, the rescuing virus in this case being VTK$^-$11.

EXAMPLE XI

Expression of HSV TK by Vaccinia Mutant VP-2 and the Use of IDC* for Identification Thereof The virus product obtained in Example X by the in vivo recombination of S-variant vaccinia virus and the calcium orthophosphate precipitate of pDP-137 Hind III digested DNA was plated out on confluent monolayers of CV-1 cells present on approximately twenty 6 cm Petri dishes at a concentration giving approximately 150 plaques per dish. The plaques were covered with a liquid overlay medium, e.g. Eagle's Special medium containing 10% calf serum. After 24 to 48 hours of incubation at 37° C. in a $CO_2$-incubator, the liquid overlay medium was removed from the dishes and replenished in each case with 1.5 ml of the same liquid overlay medium containing 1–10 μCi of $^{125}$I iododeoxycytidine (IDC*). The plates were then further incubated overnight, at 37° C. in an enriched $CO_2$ atmosphere, after which the cell monolayer present thereon was stained by the addition of Neutral red to visualize the plaques by contrast.

The medium was then removed by aspiration, the monolayers were washed three times with phosphate-buffered saline solution, and the cell monolayer on each of the plates was imprinted onto a corresponding nitrocellulose filter. The latter was exposed to X-ray film for from 1 to 3 days and then developed.

Those viral plaques containing and expressing the HSV TK gene will phosphorylate IDC* and incorporate it into their DNA, rendering the DNA insoluble. Other, unphosphorylated and unincorporated, IDC* was removed by washing, so that plaques darkening the X-ray film are those expressing recombinant HSV TK gene. Neither CV-1 cells nor vaccinia, although containing TK, will phosphorylate and incorporate IDC* in the selective fashion characteristic of the HSV TK.

After the recombinant organisms has been identified by radioautography, filter plugs were cut from the nitrocellulose filter, placed in 1 ml of overlay medium, (Eagle's Special, 10% calf serum), sonicated, and replated on CV-1 monolayers. The IDC* assay was then repeated further to purify the viral isolates. In this manner, a virus identical to the VP-2 mutant identified by hybridization in Example X was isolated by a technique dependent on the expression of the HSV TK gene present therein.

Again, the results of this Example demonstrate the expression of the HSV TK gene, present in the recombinant organisms according to the present invention, by certain of those organisms.

Those vaccinia mutants derived from pDP 137, namely VP-2, VP-4, and VP-6, all will express the HSV TK gene present therein by phosphorylation and incorporation of IDC* in the manner described above. However, the variants VP-1, VP-3, and VP-5, derived from pDP 132, will not so express the gene, possibly because the orientation of the gene within the virus is contrary to the direction of gene transcription.

EXAMPLE XII

The use of a Selective Medium for the Identification and Isolation of Recombinant Virus Containing HSV TK Gene Viruses prepared according to Example X by the in vivo recombination, in BHK-21 (C-13) cells, of VTK$^-$79 vaccinia virus and a calcium orthophosphate precipitate of pDP 137 were used to infect human (line 143) TK$^-$cells. More in particular, cell monolayers, in five Petri dishes 6 cm in diameter, were each infected with the virus of Example X at a dilution of the virus from $10^0$ to $10^{-4}$ in the presence of selective MTAGG medium. The infection technique was as described earlier.

Five well-separated plaques were isolated and one was replated on CV-1 monolayers for a second cycle of plaque purification. One further well-separated plaque, purified twice by plaque purification, was chosen and analyzed. A well-isolated plaque, thus twice plaque-purified, was selected and analyzed for the presence of the HSV TK gene by in situ hybridization employing $^{32}$P-labelled Bam HSV TK. The hybridization technique was, again, as described earlier. The mutant vaccinia virus, positive for the presence of the HSV TK gene, was denominated VP-4.

EXAMPLE XIII

Construction of pDP 120

About 20 micrograms of pDP 3 were digested with Pst I and the fragments obtained were separated on an agarose gel in a procedure analogous to that discussed in detail in Example I. The Pst I fragment having a molecular weight of 3.7 md, corresponding to the middle portion of the vaccinia Hind III F-fragment, was isolated.

Approximately 500 nanograms of this fragment were then ligated with 250 ng of pBR 322, previously cleaved with Pst I, in 20 microliters of O'Farrell buffer (OFB) [cf. O'Farrell et al., Molec. Gen. Genetics 179, 421–435 (1980)]. The buffer comprises 35 mM of tris acetate (pH 7.9), 66 mM of potassium acetate, 10 mM of magnesium acetate, 100 μg/ml of bovine serum albumin, and 0.5 mM of dithiothreitol. For purposes of ligation, 1 mM of adenosine triphosphate (ATP) and approximately 20 units of T4 D ligase (New England Biolabs) were present. The mixture was maintained at 16° C. for 16 hours.

The ligation mixture was then used to transform competent E. coli HB 101. Amp$^S$, Tet$^R$ recombinants were selected on appropriate antibiotic plates, analogous to the procedure described in Example III. Several recombinant plasmids were then analyzed by restriction analysis with Pst I and Bam HI, as in Example VII, to confirm their construction. One colony containing a plasmid with the correct construction was grown on a large scale and recovered as in Example IV and was designated pDP 120.

EXAMPLE XIV

Construction of pDP 301 A and 301 B; Construction of VP 7 and VP 8

Approximately 10 micrograms of plasmid pDP 3 were cleaved with Hind II and the 8.6 md vaccinia F-fragment was isolated in an amount of approximately 5 micrograms from an agarose gel using a technique analogous to that discussed in Example I. The fragment was self-ligated by incubating for 16 hours at 16° C. in 1.0 ml of O'Farrell buffer (OFB) containing 1 mM ATP and 80 units of T4 DNA ligase.

After incubation, the reaction was terminated by heating at 65° C. for ten minutes and the DNA was then precipitated with ethanol.

The self-ligated Hind III F-fragment was then resuspended in 250 μl of OFB and digested for four hours with 30 units of Bam HI. The reaction was terminated by heating at 65° C. for ten minutes and the resultant DNA fragments were separated on a one percent agarose gel. The band corresponding to the 8.6 md Hind III F-fragment, which fragment had been inverted around the Bam HI site, was then isolated using techniques previously described.

This inverted Hind III F-fragment was then inserted into the Bam HI site of pBR 322 as follows.

pBR 322 was cleaved with Bam HI by conventional techniques. The linear plasmid was then treated with calf intestine alkaline phosphatase (CIAP) to remove the 5'-phosphates, thus discouraging re-circularization [Chaconas et al., Methods in Enzymol. 65, 75 (1980)]. More in particular, 5 μg of linear pBR 322 in 400 μl of OFB, adjusted to pH 9.0, were combined with 0.75 units of CIAP (Boehringer Mannheim) for 30 minutes at 37° C. A further 0.75 unit of CIAP was added and the mixture digested for 30 minutes at 60° C. The DNA was then deproteinized by phenol extraction as described in Example I for the purification of vaccinia DNA.

About 450 ng of the pBR 322 DNA treated as above were then ligated to about 400 ng of inverted Hind III F-fragment in 15 μl of OFB containing 1 mM ATP and 20 units of T4 DNA ligase at 16° C. over a period of 16 hours. The ligation mixture was then used directly to transform E. coli HB 101 cells as previously described in Example III. The transformed bacteria were then screened for Amp$^R$, Tet$^S$ recombinants by plating on appropriate antibiotic plates, again as described in Example III.

The recombinant plasmids were screened by Hind III restriction analysis of minilysates (again as described in Example III) to determine which of the plasmids contained an inverted Hind III F-fragment in either orientation. Those two plasmids containing the fragment in different orientations were designated respectively as pDP 301 A and pDP 301 B.

These plasmids were used to construct two new recombinant vaccinia viruses each containing pBR 322 DNA sequences inserted into the Bam HI site of the vaccinia Hind III F-fragment in opposite orientations.

More in particular, pDP 301 A and pDP 301 B were inserted into VTK$^-$79 by in vivo recombination, as described in Example X. However, 10 μg of donor DNA (either pDP 301 A or pDP 301 B, digested with Sst I) and 2 μg of VTK$^-$79 carrier DNA were used to prepare the calcium ortho-phosphate precipitate which was employed for addition to CV-1 cells which were infected with VTK$^-$79 as the rescuing virus.

The recombinant viruses were then screened by using the replica filter technique ao disclosed in Example X using nick-translated pBR 322 DNA as the probe.

The virus in which pBR 322 DNA sequences from pDP 301 A had been recombined in vivo with VTK$^-$79 was designated as VP 7: the recombinant virus containing pBR 322 DNA from pDP 301 B was designated as VP 8.

EXAMPLE XV

Construction of pJZ 102 A/F; Construction of VP 9

A plasmid containing the complete cDNA sequence coding for the hemagglutinin (HA) gene of the influenza virus A/PR/8/34, inserted into pBR 322, is one of the plasmids made by Bacz et al. in Nucleic Acids Research 8, 5845–5858 (1980). The plasmid contains the complete nucleotide coding sequence for the HA gene inserted at the Hind III site of pBR 322.

The hemagglutinin sequence in the plasmid was switched in direction by digesting about 500 ng of the original plasmid, designated pJZ 102 A, with Hind III in OFB, then religating using T4 DNA ligase and ATP as previously described.

The ligation mixture was then used to transform competent E. coli and the bacteria were screened for Amp$^R$, Tet$^S$ colonies. Recombinant plasmids from minilysis preparations were then screened for hemagglutinin sequences present in opposite orientations by Ava I digestion of the plasmids and analysis on agarose gels. Those plasmids in which the HA sequence was present in a direction opposite to that found in pJZ 102 A were designated pJZ 102 B (cf. FIG. 9A).

Approximately 500 ng of pJZ 102 A were linearized by digestion with Bam HI in OFB as previously described. The linearized pJZ 102 A was ligated with approximately 500 ng of inverted Hind III F-fragment, the latter being conveniently obtained by Bam HI digestion of pDP 301 A (cf. Example XIV). Ligation took place in 20 μl of OFB containing 1 mM of ATP and approximately 20 units of T4 DNA ligase at 16° C. over a period of 16 hours.

The ligation mixture was used directly to transform competent E. coli RR 1 cells [Bolivar et al, Gene 2, 95–113 (1977)] as previously described.

Transformed cells were plated on ampicillin plates and screening for recombinants was effected by colony hybridization using nick-translated vaccinia Hind III F-fragment DNA as the probe, all as previously described in Example VI.

DNA from colonies found by hybridization to be positive was then analyzed by Hind III restriction analysis and agarose gel electrophoresis.

A plasmid containing pJZ 102 A inserted into the Bam HI site of vaccinia Hind III F-fragment was isolated and designated as pJZ 102 A/F.

Using the in vivo recombination technique described in detail in Example XV, 10 μg of circular donor DNA from pJZ 102 A/F were used for recombination, together with 2 μg of VTK$^-$79 carrier DNA, into VTK⁻79 vaccinia virus. Recombinant viruses were screened by the replica filter technique using a nick-translated Hind III HA fragment as the probe. The recombinant virus thus isolated was designated as VP 9.

EXAMPLE XVI

Construction of VP 10

Plasmid pJZ 102 B (cf. FIG. 10A) was inserted into VP 7 by in vivo recombination using the standard protocol employing 10 μg of circular donor pJZ 102 B DNA, 2 μg of VTK−79 carrier DNA, and CV-1 cells. Screening for recombinant viruses cntaining HA sequences was by the replica filter technique already described herein, using a nick-translated Hind III HA fragment as the probe.

A positive plaque was isolated, plaque purified, and designated as VP 10.

EXAMPLE XVII

Determination of the Expression of the HA Gene by VP 9 and VP 10

Two 6 cm petri dishes containing BHK-21 cells in a nutrient medium were infected with about 200 pfus of A/PR/8/34 influenza virus. Another pair of 6 cm petri dishes containing a monolayer of CV-1 cells in a nutrient medium were infected with about 200 pfus of VP 9 vaccinia variant, and a third pair of 6 cm petri dishes containing a CV-1 monolayer in a nutrient medium were infected with, again, about 200 pfus of VP 10.

The vuses were grown for 48 hours at 37° C. and were stained with Neutral red for one hour at 37° C. to visualize the plaques. The nutrient medium was then aspirated and the cell monolayers were washed three times with phosphate buffered saline (PBS) containing 1 mg/ml of bovine serum albumin (BSA).

1.5 ml of PBS-BSA containing 5 μl of H1 HA rabbit antiserum were next added to one of each of the three pairs of petri dishes and the dishes were incubated for one hour at room temperature. A second set of three cell cultures (one BHK and two CV-1 cultures) were treated with 1.5 ml of PBS-BSA containing 5 μl of H3 HA rabbit antiserum and again incubated for one hour at room temperature.

Next, all of the cell monolayers were washed three times with PBS-BSA and then 1.5 ml of PBS-BSA containing approximately 1 μCi of $^{125}$I-labelled protein A (New England Nuclear) was added to each of the 6 petri dishes. The dishes were then incubated for approximately 30 minutes at room temperature and the radioactive material was aspirated. The cell monolayers were washed five times with PBS-BSA. The cell monolayer on each of the six plates was then imprinted onto a corresponding nitrocellulose filter and the latter were exposed to X-ray film for from one to three days. The film was then developed.

The radioautographs showed complex formation in that petri dish in which the BHK cell monolayer had been infected with A/PR/8/34 and treated with H1 HA antiserum. Similarly, exposed film was found for the CV-1 cell monolayer infected with VP 9 and treated with H1 HA antiserum, also indicative of antigen-ntibody complex formation for this sample. All four other samples were negative for complex formation.

EXAMPLE XVIII

Determination of HA Expression by VP 9 in Rabbits

Two New Zealand white rabbits were each infected with 4 OD (at $A_{260}$) units of purified VP 9 mutant vaccinia virus either intravenously (IV) (rabbit No. 1) or intramuscularly (IM) (rabbit No. 2).

Each rabbit was bled and antiserum collected before infection (preimmune serum) and at 17 days, 25 days, and 41 days after infection. Antiserum from each rabbit was tested for its ability to neutralize vaccinia virus infection as follows.

Serial dilutions of the antisera were prepared in standard virus plaqueing medium (Eagles's special medium containing 2% of fetal bovine serum), then mixed with an equal volume of infectious vaccinia virus (100–300 pfus). Each mixture was held at 4° C. overnight, then used to infect CV-1 monolayers in 60 mm petri dishes as previously described. Specific vaccinia neutralizing antibodies present in the serum were indicated by a reduction in the total number of plaques formed. The results of such an assay are shown in following Table II.

TABLE II

Measurement of Vaccinia Neutralizing Antibodies Induced by VP 9 in Rabbits

| Approximate Plaque Reduction [% of control] | Final Dilution of Antiserum Giving Indicated Plaque Reduction: Rabbit No. 1 (IV) | Rabbit No. 2 (IM) |
|---|---|---|
| | 17 days | |
| 50% | 1:64000 | 1:16000 |
| 90% | 1:10000 | 1:2000 |
| | 25 days | |
| 50% | 1:128000 | 1:8000 |
| 90% | 1:32000 | 1:2000 |
| | 41 days | |
| 50% | 1:128000 | 1:16000 |
| 90% | 1:32000 | 1:2000 |

As a control, preimmune antiserum ast a 1:20 dilution, or no antiserum, gave approximately 180 plaques in the above assay for rabbit No. 1 and 240 plaques for rabbit No. 2.

A $^{125}$I protein A assay was performed as described in Example XVII. More in particular, three monolayers of BHK-21 cells infected with A/PR/8/34 serum were treated with 25 μl of either anti-A/PR/8/34 serum, anti-vaccinia serum, or anti-VP 9 serum from the 41-day bleeding of rabbit No. 1.

Washing and treatment with $^{125}$I protein A of each monolayer was as described in Example XVII.

Similarly, three monolayers of cells infected with vaccinia virus (S-variant) were treated with the same three antiserum preparations and also reacted with $^{125}$I protein A as previously described.

The results are presented in the following Table III and indicate that VP 9 can elicit production, by a rabbit, of antibodies to influenza hemagglutinin expressed by VP 9.

TABLE III

| Antiserum | BHK Cells Infected with A/PR/8/34 | CV-1 Cells Infected with Vaccinia Virus (S-variant) |
|---|---|---|
| Anti-A/PR/8/34 | + | − |
| Anti-vaccinia | − | + |

TABLE III-continued

| Antiserum | BHK Cells Infected with A/PR/8/34 | CV-1 Cells Infected with Vaccinia Virus (S-variant) |
|---|---|---|
| Anti-VP 9 | + | + |

The production of HA antibodies by a VP 9-infected rabbit was also tested by measurement of the hemagglutinin inhibition (HI) titer.

Namely, HI tests were performed on the preimmune, 25 day, and 41 day serum from rabbit No. 1 (IV) according to standard protocol described in detail in "Advanced Laboratory Techniques for Influenza Diagnosis, Immunology Series No. 6, Procedural Guide 1975", U.S. Dept. HEW, Public Health Service, Center for Disease Control, Bureau of Laboratories, Atlanta, Ga.

Table IV below shows the HI titers determined using 3+ HA units with the various antisera tested. Extracts of BHK cells infected with A/PR/8/34 influenza virus were used as a source of HI hemagglutinin.

TABLE IV

| Antiserum | Hemagglutinin Inhibition | Titer |
|---|---|---|
| Anti-A/PR/8/34 | greater than | 1:320 |
| Preimmune serum | less than | 1:10 |
| 25 day antiserum | | 1:60 |
| 41 day antiserum | greater than | 1:320 |

EXAMPLE XIX

Construction of pDP 250 A and 250 B. Construction of VP 11 and VP 12

A plasmid pTHBV 1 can be constructed by the methods described by Hirschman et al., Proc. Natl. Acad. Sci. USA 77, 5507–5511 (1980), Christman et al., Proc. Natl. Acad. Sci. USA 79, 1815–1819 (1982).

About 20 micrograms of the pTHBV 1 plasmid containing two HBV genomes (subtype ayw) in a head-to-tail arrangement inserted into the Eco R1 site of pBR 322 were cleaved with Bgl II restriction endonuclease.

The fragments were separated on a 1.0 percent agarose gel and a 1.5 md fragment of HBV DNA sequences coding for the HBV surface antigen and pre-surface antigen was isolated (cf. Galibert et al., op. cit.).

About 500 ng of pDP 120 were partially digested with Bam HI under conditions similar to those described in Example V earlier herein.

The resulting digest was then treated with calf intestine alkaline phosphatase (CIAP) in a manner analogous to that described earlier herein in Example XIV. Finally, the aforementioned fragment of gl II-cleaved pTHBV 1 plasmid was ligated into the Bam HI site of the CIAP-treated pDP 120 Bam HI digest under conditions similar to those described earlier herein.

The ligation mixture was used directly to transform competent E. coli RR 1 cells, also as previously described.

The resulting Amp$^S$, Tet$^R$ colonies were screened for recombinant plasmids by digesting minilysates of possible recombinants with Xho I and Pst I and analyzing on an agarose gel.

Two recombinant plasmids were isolated, corresponding with insertion, into the Bam HI site present in the vaccinia portion of pDP 120, of the HBV Bgl II fragment in each of two possible directions. The plasmids were designated as pDP 250 A and pDP 250 B (cf. FIG. 11).

Finally, recombinant vaccinia viruses containing the HBV surface antigen and presurface antigen sequences were constructed by in vivo recombination (see Example X) using 20 μg each of either circular pDP 250 A or pDP 250 B and 2 μg of VTK−79 carrier DNA, with VTK−79 as the infecting virus, all as previously described.

The viruses were screened for recombinants using the replica filter technique with nick-translated pTHBV DNA as a probe.

The resulting recombinant vaccinia viruses containing the Bgl II fragments of HBV virus in one of two directions were designated as VP 11 and VP 12, as shown in FIGS. 11D and E. (The normal direction of HBV transcription is indicated for the plasmids in FIG. 11D.)

EXAMPLE XX

Construction of pDP 252; Construction of VP 13

20 μg of plasmid pTHBV 1 (cf. Example XIX) were digested with Hha I restriction endonuclease. The largest fragment of the Hha I digest comprises 1084 base pairs and contains that entire sequence of the hepatitis B virus coding for the surface antigen, without the region coding for the pre-surface antigen (cf. Galibert et al., op. cit.)

This fragment was inserted into pBR 322 at the Hind III site using Hind III linkers. More in particular, approximately 400 ng of HBV Hha I fragment, isolated from a preparative gel as previously described, were treated with six units of T4 DNA polymerase (P/L Biochemicals) present in 40 μl of OFB also containing 2 mM each of deoxyadenosine triphosphate (dATP), deoxyguanidine triphosphate (dGTP), deoxycytosine triphosphate (dCTP), and deoxythymine triphosphate (dTTP). The mixture was incubated at 37° C. for 30 minutes to trim the extending 3'-ends of the fragment, generated by Hha I restriction endonuclease (cf. O'Farrell et al., op. cit.)

After the reaction period, approximately 500 ng of phosphorylated Hind III linkers (Collaborative Research), 2.5 μl of 20 mM adenosine triphosphate, 1 μl of 100 mM spermidine (Cal Biochem.), and 1 μl (approximately 80 units) of T4 DNA ligase were added and incubation was continued at 10° C. for sixteen hours.

The reaction was stopped by heating at 65° C. for ten minutes and 400 ng of pBR 322 were added.

The Hind III linkers and pBR 322 were then cleaved by adding approximately 20 units of Hind III and digesting the mixture at 37° C. for four hours.

Once more, the reaction was stopped by heating at 65° C. for ten minutes and the unligated linkers were removed by spermine precipitation according to Hoopes et al., Nucleic Acids Research 9, 5493 (1981).

More specifically, 2.5 μl of 0.2M spermine in H$_2$O were added to the reaction mixture to make it 10 mM in spermine. The reaction mixture was incubated on ice for 15 minutes and the precipitate which formed was collected by centrifugation. Residual spermine was removed from the DNA by resuspending the DNA pellet in 75 percent ethanol, 0.3M sodium acetate, and 10 mM of magnesium acetate. This mixture was incubated on ice for 60 minutes. Residual spermine dissolves in the ethanol, leaving a suspension of DNA which was again pelleted by centrifugation and redissolved in 20 μl of OFB containing 1 mM of ATP and approximately 20 units of T4 DNA ligase. Ligation of the pBR 322 and Hind III-linked fragment was carried out for 16 hours at 10° C.

The ligation mixture was then used directly to transform competent E. coli RR1 cells as previously described. The transformants were plated onto ampicillin plates and screened by colony hybridization as previously described herein. A nick-translated HBV Hha I fragment was used as the probe.

Colonies proved positive by hybridization were analyzed by restriction digestion of minilysates. A plasmid containing the Hha I fragment, inserted at the Hind III site, was characterized and designated as pDP 252.

A recombinant vaccinia virus containing the Hha I HBV fragment coding for the HBV surface antigen was constructed using the standard in vivo recombination protocol as set forth in Example XV using 10 μg of circular pDP 252 as the donor DNA with 2 μg of VP 8 DNA as the carrier DNA and VP 8 as the infecting virus for CV-1 cells.

The viruses were screened for recombinants using the replica filter technique with a nick-translated Hha I HBV fragment as the probe.

The resulting recombinant virus was designated as VP 13.

EXAMPLE XXI

Construction of pBL 520 A and 520 B; Construction of VP 14 and VP 16

Approximately 20 μg of herpes virus type I, strain KOS, DNA, extracted as described by Pignatti et al., Virology 93, 260–264 (1979) were digested with Eco RI and the resulting fragments were separated on an agarose gel. Eco RI fragment F was isolated from the gel by conventional techniques.

About 200 ng of the Eco RI fragment F were ligated with 60 ng of pBR 322, digested with Eco RI and subsequently treated with calf intestine alkaline phosphatase in a manner described earlier herein in Example XIV. The CIAP treated pBR 322 and the Eco RI F-fragment were ligated in 20 μl of OFB containing 1 mM of ATP and approximately 80 units of T4 DNA ligase at 16° C. over a period of 16 hours.

The entire ligation mixture was used to transform competent E. coli RR I cells as described in earlier Examples.

The transformed E. coli were grown on ampicillin plates and the Amp$^R$, Tet$^R$ transformed E. coli were screened for recombinant plasmids by restriction analysis of minilysates as previously described. Restriction analysis was done with Hpa I and Eco RI to determine the orientation of the insertion of the Eco RI F-fragment in the plasmid.

The two plasmids thus obtained having the HSV Eco RI F-fragment inserted into pBR 322 in each of two opposite orientations were designated pBL 520 A and pBL 520 B, as shown in FIG. 13B.

Two new vaccinia recombinants, VP 14 and VP 16, were constructed by in vivo recombination techniques described in Example X and XV using these plasmids and VP 7. More specifically, 20 μg each of pBL 250 A or pBL 250 B, 2 μg of VP 7 carrier DNA, and VP 7 virus were used to treat CV-1 cells to effect the in vivo recombination. Recombinant viruses were screened by the replica filter technique using nick-translated HSV Eco RI F-fragment as the probe.

EXAMPLE XXII

Construction of pBL 522 A and 522 B; Construction of VP 17 and VP 18

Approximately 20 μg of pBL 520 A (cf. Example XXI) were digested with Bam HI and the resulting fragments separated on an agarose gel. A 5.1 md fragment corresponding with the Bam HI G-fragment of HSV DNA (strain KOS) was isolated from the gel using techniques such as those described in Example I.

Plasmid pDP 120 was partially digested with Bam HI to linearize the plasmid using techniques analogous to those described previously in Example V. The digested plasmid was further treated with calf intestine alkaline phosphatase as in Example XIV to prevent recirculation.

Approximately 100 ng of the pDP 120 DNA so treated were ligated with 120 ng of the previously described Bam HI G-fragment in 20 μl of OFB containing 1 mM ATP and approximately 80 units of T4 DNA ligase at 16° C. over a period of 16 hours.

Thereafter, the ligation mixture was used directly to transform competent E. coli RR I cells as described in previous Examples.

The transformed E. coli were then screened for Amp$^S$, Tet$^R$ recombinants by colony hybridization as previously described using HSV Eco RI fragment as the probe. Colonies positive by hybridization were screened by restriction analysis of minilysates with Bam HI and Sst I to determine if the complete HSV Bam HI G-fragment had been inserted and to determine its orientation within the resulting plasmid.

Two recombinant plasmids were found in this way, each containing the HSV Bam HI G-fragment in opposite orientations in the parent plasmid pDP 120. The new plasmids were designated pBL 522 A and pBL 522 B.

Again using the in vivo recombination technique described in detail in Examples X and XV herein, 20 μg of donor pBL 522 A or B were respectively combined with 2 μg of carrier VTK$^-$79 DNA to form a calcium orthophosphate precipitate. This and the vaccinia virus VTK$^-$79 were used to treat CV-1 cells, with the production of two virus mutants designated as VP 17 and VP 18, respectively.

The vaccinia mutants were identified using the relica filter technique with HSV Eco RI F-fragment as probe.

EXAMPLE XXIII

Construction of an L-variant TK$^-$ Vaccinia Virus from the TK$^-$ S-variant

In wild-type vaccinia virus, the vaccinia TK gene is known to be present in the Hind III J-fragment [Hruby et al., J. Virol. 43, 403–409 (1982)]. Hence, the Hind III J-fragment of the TK$^-$79 S-variant vaccinia virus of Example VIII must have a mutation in the TK gene which inactivates the gene.

A TK$^-$ L-variant vaccinia virus was derived in the following manner using the Hind III J-fragment of the TK$^-$79 S-variant.

The Hind III J-fragment of TK$^-$79 was inserted into pBR 322 in a manner like that for the Hind III F-fragment in Example II. The resulting plasmid was used in the standard in vivo recombination protocol, specifically using 10 μg of the plasmid donor DNA, 2 μg of L-variant vaccinia DNA as carrier, and L-variant vaccinia virus-infected CV-1 cells.

Progeny virus was used to infect human TK⁻ cells (line 143) (earlier described) in the presence of 40 μg of BUdR. Virus which grew was plaque purified in the presence of BUdR and virus from a single plaque was chosen and designated VTK−79 L (ATCC No. VR2056). It cannot be determined whether the new virus is a spontaneous mutation or is a recombinant containing the J-fragment of the TK−79 S-variant: the latter is more likely.

EXAMPLE XXIV

Construction of pDP 202

About 34 μg of L-variant vaccinia virus DNA was digested to completion in Ava I buffer [20 mM tris-HCL (pH 7.4), 30 mM Nacl, 10 mM MgCl$_2$] with Ava I restriction endonuclease and the resulting fragments were separated on an agarose gel as previously described. The Ava I H-fragment was then isolated from the agarose gel.

Approximately 400 ng of pBR 322 in 50 μl of Hind III buffer were digested to completion with Hind III. Reaction was terminated by heating at 65° C. for 10 minutes, at which time 45 μl (approximately 600 ng) of the isolated vaccinia Ava I H-fragment were added. Then, the total mixture was precipitated with ethanol. The resulting DNA pellet was redissolved in 9.5 μl of T4 DNA polymerase buffer [20 mM tris-HCl (pH 7.6), 10 mM MgCl$_2$, 1 mM dithiothreitol, 33 μM dTTP, 33 μM dGTP, 33 μM dCTP, and 33 μM dATP]. The protruding 5'-ends of the DNA fragments were filled in by adding 1.5 units of T4 DNA polymerase and incubating at 37° C. After 30 minutes, 0.5 μl of a 0.02M solution of ATP was added to make the reaction mixture 1 mM with respect to ATP, together with 1 μl (approximately 80 units) of T4 DNA ligase. Ligation was then carried out at 10° C. for 20 hours.

The entire ligation mixture was used directly to transform competent *E. coli* HB 101.

Transformed bacteria were plated on nitrocellulose filters placed on ampicillin plates. Recombinant colonies were screened by colony hybridization using nick-translated vaccinia Ava I H-fragment as a probe.

Plasmids isolated from colonies which were positive by colony hybridization were digested with Hind III and analyzed on an agarose gel as previously described. One such plasmid which contained an Ava I H-fragment inserted at the Hind III site of pBR 322 was purified and designated pDP 202. Further characterization of this plasmid by restriction analysis with Sst I and Bam HI determined the orientation of the fragment within the plasmid (cf. FIG. 15A).

EXAMPLE XXV

Construction of Plasmids pDP 202 TK/A-F; Construction of VP 22

Plasmids pDP 202 TK/A-F were constructed by inserting the Bgl I/Bam HI TK fragment of HSV into each of the three Bam HI sites in the vaccinia Ava I H-fragment portion of pDP 202. The Bgl II/Bam HI fragment contains the coding region for the HSV TK gene, but not the associated HSV promoter sequence [McNight et al., Cell 25, 385-398 (1981)].

This was accomplished first by isolating a linear pDP 202 plasmid (7.3 md) which had been linearized at a Bam HI site by partial digestion of the plasmid with Bam HI. The Bgl II/Bam HI TK fragment was prepared by digesting the HSV Bam TK plasmid (cf. Example V) with Bgl II and Bam HI. Bgl II digestion cleaves the Bam HI TK fragment at one site, resulting in a 1.8 md fragment containing the coding region of the TK gene and a 0.5 md fragment corresponding to the 5'-end of the Bam HI TK fragment containing the HSV promoter. The 1.8 md Bgl II/Bam HI fragment was isolated from an agarose gel.

To construct the plasmids pDP 202 TK/A-F, approximately 500 ng of Bam HI linear pDP 202 which had been treated with CIAP as previously described was ligated with 250 ng of the aforementioned Bgl II/Bam HI TK fragment in 20 μl of OFB containing 1 mM ATP and approximately 100 units of T4 DNA ligase at 16° C. for 16 hours. The entire ligation mixture was then used to transform competent *E. coli* RR I cells as previously described. Transformed cells were plated on ampicillin plates and the colonies were screened for recombinant plasmids by restriction analysis of minilysates with Bam HI to determine at which Bam HI site the Bgl II/Bam HI TK fragment was inserted, and in which orientation. The site and direction of orientation were confirmed by restriction analysis with Sst I. By this procedure, the Bgl II/Bam HI TK fragment was found to be inserted into each of the three Bam HI sites in the vaccinia Ava I H-fragment in both orientations. Each plasmid pDP 202 TK was given a letter designation from A to F (cf. FIG. 15C.).

Preparative amounts of plasmids were then grown and purified and used to construct recombinant viruses using the standard in vivo recombination protocol of Example X and XV. That is, approximately 20 μg of donor DNA from each recombinant plasmid were mixed with 2 μg of VTK−79 DNA as a carrier and were added, in the form of a calcium phosphate precipitate, to a monolayer of CV-1 cells infected with VTK−79 L virus. Recombinant viruses were screened by using the replica filter technique earlier described using nick-translated HSV Bam TK DNA as a probe.

One recombinant virus which was isolated from in vivo recombination of VTK−79 L and pDP 202 TK/E was isolated and designated as VP 22. This mutant virus was of particular interest because it induced a higher level of HSV TK activity in infected cells than does VP 2, VP 4, or VP 6 (earlier described herein) as measured by a $^{125}$I-iododeoxycytidine assay (IDC*).

More in particular, L-variant vaccinia, VP 4, and VP 22 were used to infect monolayers of CV-1 cells at the appropriate dilutions to yield 200 plaques per 60 mm Petri dish. Each dish was then treated with $^{125}$I IDC and washed as previously described in Example XI to compare the levels of HSV TK activity.

Infected cell monolayers were then lifted onto nitrocellulose filters which were placed on a single sheet of X-ray film to compare the levels of TK activity by comparing the relative exposure (darkening) of the film by each filter.

The results of the IDC* assay indicated that L-variant vaccinia contained no HSV TK activity and therefore did not expose the film. VP 4, shown earlier in Example XI to contain HSV TK activity, caused a faint darkening of the film; VP 22 caused 15-20 times the exposure of VP 4, indicating a significantly higher level of HSV TK activity.

What is claimed is:

1. A recombinant vaccinia virus synthetically modified by the presence, in a non-essential region of the vaccinia genome, of DNA not naturally occurring in vaccinia virus.

2. A vaccinia virus as in claim 1 wherein said DNA is expressed in a host by the production of a protein.

3. A vaccinia virus as in claim 2 wherein said protein is an antigen.

4. A vaccinia virus as in claim 2 wherein said DNA is a gene of herpes simplex expressed in a host by the production of thymidine kinase.

5. A vaccinia virus as in claim 4 wherein said virus is free of vaccinia gene producing thymidine kinase.

6. A vaccinia virus as in claim 3 wherein said antigen is influenza virus hemmagglutinin.

7. A vaccinia virus as in claim 1 which is vaccinia virus VP-2, VP-3, VP-4, VP-5, VP-6, VP-7, VP-8, VP-9, VP-10, VP-11, VP-12, VP-13, VP-14, VP-16, VP-17, VP-18, or VP-22.

8. A recombinant vaccinia virus as in claim 1 wherein said DNA not naturally occurring in vaccinia virus has been introduced into said virus by in vivo recombination.

9. A modified vaccinia virus as in claim 1 wherein said DNA not naturally occurring in vaccinia virus includes viral DNA.

10. A modified vaccinia virus as in claim 1 wherein said DNA not naturally occurring in vaccinia virus includes bacterial DNA.

11. A modified vaccinia virus as in claim 1 wherein said DNA not naturally occurring in vaccinia virus includes synthetic DNA.

12. A biologically pure culture of a vaccinia virus selected from the group consisting of VTK$^-$79 and VTK$^-$79 L.

* * * * *

UNITED STATES PATENT AND TRADEMARK OFFICE
CERTIFICATE OF CORRECTION

PATENT NO. : 4,603,112            Page 1 of 2
DATED     : July 29, 1986
INVENTOR(S) : Enzo Paoletti and Dennis Panicali It is certified that error appears in the above–identified patent and that said Letters Patent are hereby corrected as shown below:

The title page should be deleted to appear as per attached title page.

Signed and Sealed this

Fourth Day of November, 1986

[SEAL]

*Attest:*

DONALD J. QUIGG

*Attesting Officer*    *Commissioner of Patents and Trademarks*

United States Patent [19]

Paoletti et al.

[11] Patent Number: 4,603,112

[45] Date of Patent: Jul. 29, 1986

[54] MODIFIED VACCINIA VIRUS

[75] Inventors: Enzo Paoletti, Delmar; Dennis Panicali, Averill Park, both of N.Y.

[73] Assignee: Health Research, Incorporated, Albany, N.Y.

[21] Appl. No.: 446,824

[22] Filed: Dec. 8, 1982

Related U.S. Application Data

[63] Continuation-in-part of Ser. No. 334,456, Dec. 24, 1981.

[51] Int. Cl.$^4$ .................. C12N 7/00; C12N 15/00
[52] U.S. Cl. .................. 435/235; 435/172.1; 435/172.2; 435/172.3; 424/89
[58] Field of Search .......... 435/235, 238, 172.1, 435/172.2, 172.3

[56] References Cited

PUBLICATIONS

Panicali et al., "Two Major DNA Variants etc.", J. Virol. 37(3), 1981, 1000–1010.
Weir et al., "Mapping of the Vaccinia Virus etc.", Proc. Nat'l. Acad. Sci. USA 79, 1982, 1210–1214.
Nakano et al., "Molecular Genetics of Vaccinia etc.", Proc. Nat'l. Acad. Sci. USA 79, 1982, 1593–1596.
Panicali et al., "Construction of Poxviruses etc.", Proc. Nat'l. Acad. Sci. USA 79, 1982, 4927–4931.
Mackett et al., "Vaccinia Virus etc.", Proc. Nat'l. Acad. Sci. USA 79, 1982, 7415–7419.
Smith et al., "Infectious Vaccinia Virus Recombinants etc.", Nature 302, 1983, 490–495.
Panicali et al., "Construction of Live Vaccines etc.", Proc. Nat'l. Acad. Sci. USA 80, 1983, 5364–5368.
Ensinger et al., "Marker Rescue etc.", J. Virol. 48(2); 1983, 419–428.
Smith et al., "Construction and Characterization etc.", Proc. Nat'l. Acad. Sci. USA 80, 1983, 7155–7159.
Jones et al., "Mapping of the Vaccinia Virus etc.", J. Virol. 49(1), 1984, 72–77.
Paoletti et al., "Construction of Live Vaccines etc.", Proc. Nat'l. Acad. Sci. USA 81, 1984, 193–197.
Mocarski et al.–Cell, vol. 22, (1980) p. 243.
Morse et al.–J. Virol., vol. 26, (1978) p. 389.
Bossart et al.–Chem. Abst., vol. 89, (1978) p. 56,251n.
Katz et al.–Chem. Abst., vol. 89, (1978) p. 39,241s.
Sam et al.–Ann. Virol., vol. 132E, (1981) pp. 135–150.
Wigler et al.–Cell, vol. 11, (1977) pp. 223–232.
Moss et al.–J. of Virology, vol. 40, No. 2, Nov. 1981, pp. 387–389, & 393–395.
Shigeru et al., C.A. 86 #3119g, 1977 of Yakugaku Zasshi (1976)96(10): 1247–1254, Protein Inhibitors of Gastric Acid Secretion Isolated From Vaccinia Virus-Infected Tissues.
Shigeru, C.A. 88 #55061t, 1978 of Japan Kokai 77116402, 29 Sep. 1977, Gastric Juice Secretion–Inhibiting Protein From Vaccinia Virus Infected Animal Tissues.
Nippon Zoki Pharm. C.A. 94 #7711g, (1981) of Jpn. Kokai Tokkyo Koho 8087724, 2 Jul. 1980, Selective Immune Enhancer.
Kruczek-Juszczyk C.A. 92 #126795f, (1980) of Ann. Univ. Mariae Curie Sect. C, 1978, 33: 1–8, Interferon Induction by Viral Nucleic Acids in Chick Embryo Fibroblasts.
Panicali et al., C.A. 94 #135967g, 1981 of J. Virol., 1981, 37(3): 1000–10, Two Major DNA Variants Present in Serially Propagated Stocks of the WR Strain of Vaccinia Virus.
Katz et al., C.A. 89 #39241s, (1978) of J. Antimicrob. Chemother. 1978 4(2): 159–162, Genetic Recombination Between Temperature Sensitive Mutant and IBT Resistant Mutant of Vaccinia Virus.
Chem. Abstracts, 10th Coll. Index, (1977–1981), vols. 86–95, Virus, Animal, Vaccinia Virus.

*Primary Examiner*—Sam Rosen
*Attorney, Agent, or Firm*—Curtis, Morris & Safford

[57] ABSTRACT

What are disclosed are methods for modifying the genome of vaccinia virus to produce vaccinia mutants, particularly by the introduction into the vaccinia genome of exogenous DNA; modified vaccinia prepared by such methods; certain DNA sequences and unmodified and genetically modified microorganisms involved as intermediates in such methods; and methods for infecting cells and host animals with such vaccinia mutants to provoke the amplification of exogenous DNA and proteins encoded by the exogenous DNA, including antigenic proteins, by said cells and host animals.

12 Claims, 15 Drawing Figures